United States Patent [19]
Jayasena et al.

[11] Patent Number: 6,063,612
[45] Date of Patent: May 16, 2000

[54] ANTIVIRAL REAGENTS BASED ON RNA-BINDING PROTEINS

[75] Inventors: Sumedha D. Jayasena; Brian H. Johnston, both of Mountain View, Calif.

[73] Assignee: SRI International, Menlo Park, Calif.

[21] Appl. No.: 07/808,452

[22] Filed: Dec. 13, 1991

[51] Int. Cl.$^7$ ............................ C12N 7/00; C07K 14/00
[52] U.S. Cl. .................. 435/235.1; 530/320; 530/325; 530/826
[58] Field of Search ................... 530/826, 320, 530/325; 435/235.1

[56] References Cited

PUBLICATIONS

Malimetal 1989 Cell 58:205–214.
Corey & Schultz, 1987 Science 238:1401.
Ebright et al. 1990 PNAS 87:2882–2886.
Weeks et al. 1990 Science 249:1281.
Arnott, S. and Selsing, E., J. Mol. Biol. 88:509–521 (1974).
Beal, P.A. and Dervan, P.B., Science 251:1360–1363 (1991).
Birg, F., et al., Nucleic Acids Res. 18(10):2901–2908 (1990).
Cazenave, C., et al., Nucleic Acids Res. 15(24):10507–10521 (1987).
Chen, F.–M., Biochem. 30:4472–4479 (1991).
Cooney, M., et al., Science 241:456–459 (1988).
Cross, S., et al., Cell 49:47–56 (1987).
DeWet, J.R., et al., Mol. and Cell. Biol. 7(2):725–737 (1987).
Durand, D.B., et al., Mol. and Cell. Biol. 8(2):1715–1724 (1988).
Francois, J.–C., et al., Nucleic Acids Res. 16(24):11431–11440 (1988).
Francois, J.–C. et al., Proc. Natl. Acad. Sci. USA 86:9702–9706 (1989).
Francois, J.–C., et al., Biochem. 28:9617–9619 (1989).
Gorman, C., et al., Mol. and Cell. Biol. 2(9):1044–1051 (1982).
Griffin, L.C., and Dervan, P.B., Science 245:967–971 (1989).
Haner, R., and Dervan, P.B., Biochem. 29(42,.9762–9765 (1990).
Hanvey, J.C., et al., Nucleic Acids Res. 18(1):157 (1989).
Hausheer, F.H., et al., Anti–Cancer Drug Design 5:159–167 (1990).
Helene, C., and Thoung, N.T., Genome 31:413–421 (1989).
Helene, C., and Toulme, J.–J., Biochim. et Biophys. Acta 1049:99–125 (1990).
Horne, D.A., and Dervan, P.B., J. Am. Chem. Soc. 112:2435–2437 (1990).
Kohwi, Y., and Kohwi–Shigematsu, T., Proc. Natl. Acad. Sci. USA 85:3781–3785 (1988).
Kohwi–Shigematsu, T., and Kohwi, Y., Nucleic Acids Res. 19(15):4267–4271 (1991).
Letai, A.G., et al., Biochem. 27:9108–9112 (1988).
Lyamichev, V.I., et al., Nature 344:568 (1990).
Maher III, L.J., et al., Science 245:725–730 (1989).
Manzini, G., et al., J. Mol. Biol. 213:833–843 (1990).
Mergny, J.–L., et al., Biochem. 30(40):9791–9798 (1991).
Mirkin, S.M., et al., Nature 330:495 (1987).
Moffat, A., Science 252:1374 (1991).
Moser, H.E., and Dervan, P.B., Science 238:645–650 (1987).
Ono, A., et al., Biochem. 30:9914–9921 (1991).
Orson, F.M., et al., Nucleic Acids Res. 19(12):3435 (1991).
Pei, D., et al., Science 253:1408 (1991).
Perrouault, L., et al., Nature 344:358 (1990).
Pilch, D.S., et al., Proc. Natl. Acad. Sci. USA 87:1942–1946 (1990).
Plum, G.E., et al., Proc. Natl. Acad. Sci. USA 87:9436–9440 (1990).
Postel, E.H., et al., Proc. Natl. Acad. Sci. USA 88:8227–8231 (1991).
Praseuth, D., et al., Proc. Natl. Acad. Sci. USA 85:1349–1353 (1988).
Radhakrishnan, I., et al., Biochem. 30(87):9022–9030 (1991).
Radhakrishnan, I., et al., J. Mol. Biol. 221:1403–1418 (1991).
Rajagopal, P., and Feigon, J., Nature 339:637 (1989).
Roberts, R.W., and Crothers, D.M., Proc. Natl. Acad. Sci. USA 88:9397–9401 (1991).
Shaw, J.–P., et al., Science 241:202 (1988).
Siekevitz, M., et al., Proc. Natl. Acad. Sci. USA 84:5389–5393 (1987).
Strobel, S.A., and Dervan, P.B., Nature 35:172–174 (1991).
Sun, J.–S., et al., Proc. Natl. Acad. Sci. USA 86:9198–9202 (1989).
Williams, T., et al., J. Immunol. 141(2):652–666 (1988).
Young, S.L., et al., Proc. Natl. Acad. Sci. USA 88:10023–10026 (1991).

*Primary Examiner*—Karen Cochrane Carlson
*Attorney, Agent, or Firm*—Gary R. Fabian; Dehlinger & Associates

[57] ABSTRACT

The present invention describes the generation of site-directed RNA cleaving agents. These agents consist of RNA-binding proteins, or polypeptides derived thereof, which are modified to contain a moiety capable of cleaving RNA backbones. Alternatively, the agents are oligonucleotides having nuclease resistant backbones to which a moiety capable of cleaving RNA backbones has been attached. The present invention also describes a method of cleaving target RNA substrates using the cleaving agents described herein. Further, the invention describes a method for inhibiting RNA virus expression in infected cells.

7 Claims, 14 Drawing Sheets

HIV-1 TAR

HIV-2 TAR

Met Glu Pro Val Asp Pro Arg Leu Glu Pro Trp Lys His Pro Gly Ser Gln Pro Lys Thr Ala
Cys Thr Asn Cys Tyr Cys Lys Lys Cys Cys Phe His Cys Gln Val Cys Phe Ile Thr Lys Ala
Leu Gly Ile Ser Tyr Gly Arg Lys Lys Arg Arg Gln Arg Arg Arg Pro Pro Gln Gly
Ser Gln Thr His Gln Val Ser Leu Ser Lys Gln Pro Thr Ser Gln Ser Arg Gly Asp Pro Thr
Gly Pro Lys Glu

Fig. 2A

Arg Lys Lys Arg Arg Gln Arg Arg Arg Pro Pro Gln Gly Ser Gln Thr His Gln Val Ser Leu
Ser Lys Gln Cys-phen

Fig. 2B

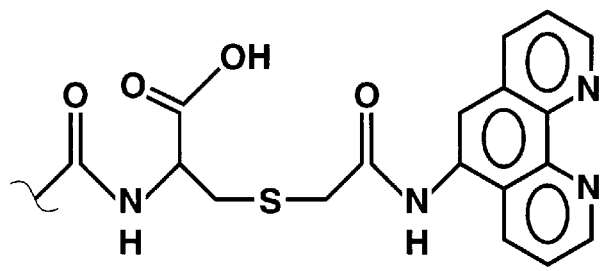

Fig. 2C

MAGRSGDSDEDLLKAVRLIKFLYQSNPPPNPEGTRQARRNRRRRWRERQRQIHSISERILSTYL
GRSAEPVPLQLPPLERLTLDCNEDCGTSGTQGVGSPQILVESPTILESGAKE
Fig. 4
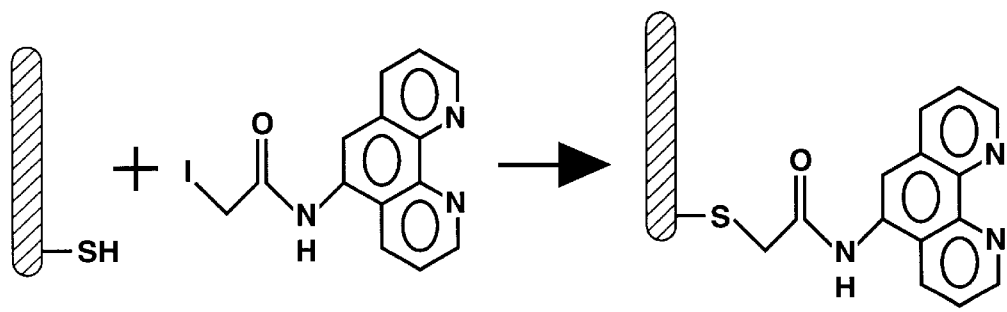
Fig. 5
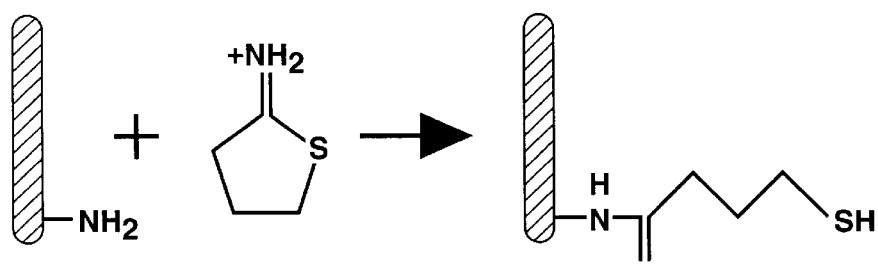
Fig. 6

5'- TTTAAAAGAAAAGGGGGGACTGG
    AAATTTTCTTTTCCCCCCTGACC-5'

5'- GCTGGGACTTTCCAGGGAGGCGT
    CGACCCTGAAAGGTCCTCCGCA-5

5'- CCTGGGCGGGACTGGGGAGTGGCGAGCCC
    GGACCCGCCCTGACCCCTCACCGCTCGGG-5

| | | |
|---|---|---|
| A-1 | 5'-AGGGGGGAAAAGAAAA | Pu·PuPy |
| A-2 | 5'-TTTTCTTTTTCCCCCT | Py·PuPy |
| B-1 | 5'-GGAGGGACCTTTCAGGGG | Pu·PuPy – Py·PuPy – Pu·PuPy – Py·PuPy |
| B-2 | 5'-CCCCTGAAAGGTCCCTCC | Py·PuPy – Pu·PuPy – Py·PuPy – Pu·PuPy |
| C-1 | 5'-GAGGGGAGAGGGGAGAGGGGGG | Pu·PuPy |
| C-2 | 5'-CCCGCCCTGACCCCTCACCGCTC | Pu·PuPy>>Py PuPy |
| K | 5'-AAAAGAAAAGGGGGA | |
| L | 5'-GGGGATCCCCTTAGGGAGG | |
| M | 5'-GGGTGGGATCGGGGAGCGGTGGAGAG | |

Fig. 12

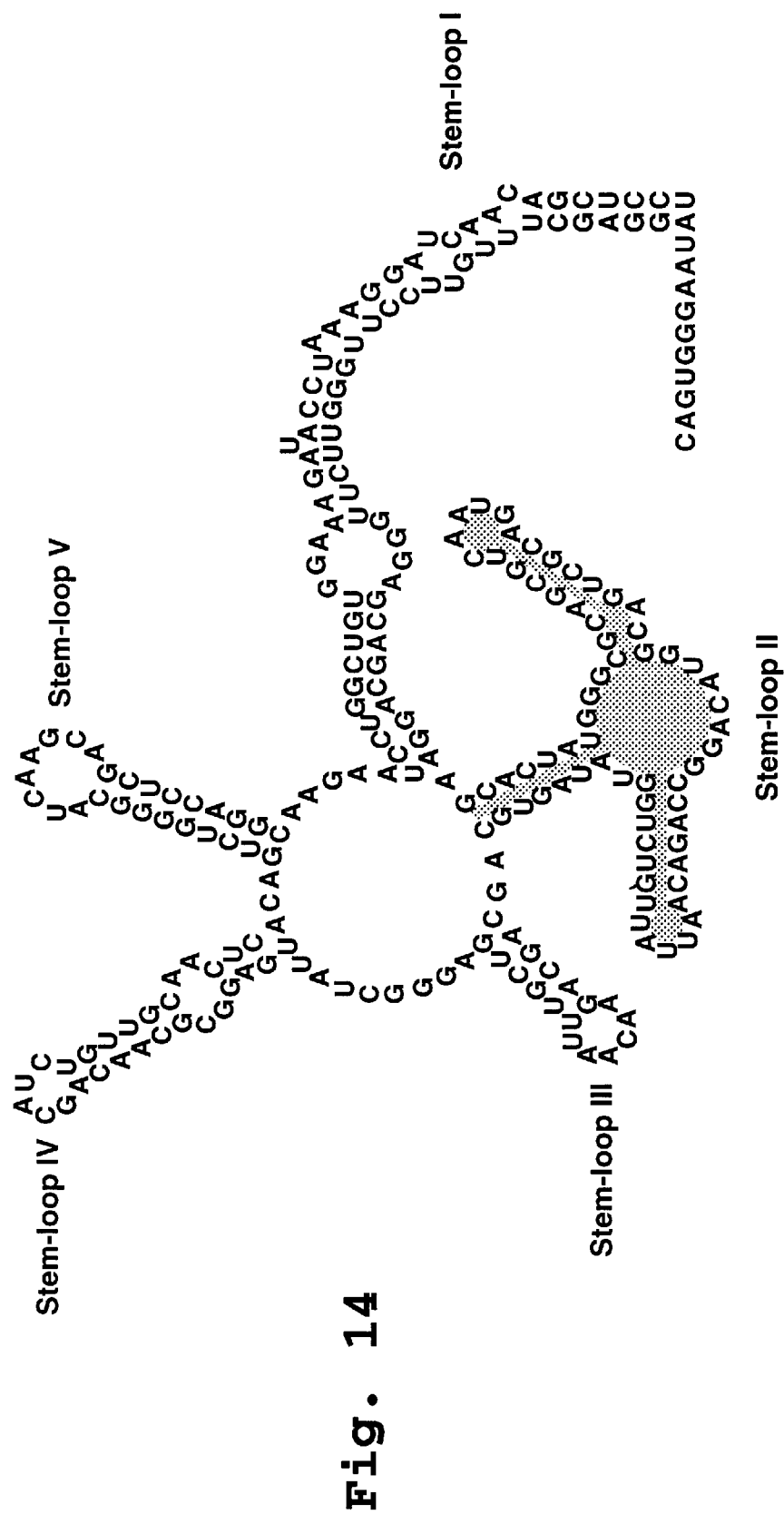

ANTIVIRAL REAGENTS BASED ON RNA-BINDING PROTEINS

FIELD OF THE INVENTION

The present invention relates to RNA-binding proteins modified to contain nucleic acid cleaving moieties, in particular, viral trans-acting proteins can be used as specific antiviral reagents. The invention further includes methods for generating said antiviral reagents, methods of cleaving viral nucleic acid, and methods of inactivating viral nucleic acid in cells.

References

Arya, S. K., et al., Science 229, 69–73, (1985).
Arya, S. K., et al., Proc. Natl. Acad. Sci. USA 83, 2209–2213, (1986).
Arya, S. K., et al., Proc. Natl. Acad. Sci. USA 85, 9753–9757 (1988).
Ausubel, F. M., et al., *Current Protocols in Molecular Biology*, John Wiley and Sons, Inc., Media Pa.
Bass, B., et al., Cell 48, 607–613 (1987).
Beal, P. A., et al., Science, 251, 1360–1363 (1991).
Berkhout, B., et al., Cell 59, 273–282, (1989).
Breslow, R., et al., Proc. Natl. Acad. Sci. USA 86, 1746–1750 (1989).
Brown, S., et al., J. Biol Chem. 265, 11238–11243 (1990).
Bruice, T. W., et al., J. Am. Chem. Soc. 113, 5446–5449 (1991).
Chen, C. B., et al., Proc. Natl. Acad. Sci. USA 83, 7147–7151 (1986).
Chen, C. B., et al., Science 237, 1197–1201 (1987).
Clavel, F., et al., Science 233, 343–346, (1986).
Clouse, K. A. et al., J. Immunol. 142, 431–438, 1989.
Cook, K. S., et al., Nucleic Acids Res. 19, 1577–1583, (1991).
Cordingley, M. G., et al., Proc. Natl. Acad. Sci. USA 87, 8985–8989 (1990).
Corey, D. R. & Schultz, P., Science 238, 1401–1403 (1987).
Crea, R., U.S. Pat. No. 4,888,286, issued Dec. 19, 1989.
Crowe, S. M., et al., AIDS Res. Hum. Retroviruses 6(8):1031 (1990).
Crowe, S. M., et al., J. Med. Virol. 29(3):176 (1989).
Daly, T. J., et al., Nature, 342, 816–819 (1989).
Davanloo, P., et al., Proc. Natl. Acad. Sci. USA 81:2035 (1984).
Dayton, A. I., et al., Cell 44, 941–947 (1986).
Dervan, P. B. Science 232, 464–471 (1986).
Dingwall, C., et al., Proc. Natl. Acad. Sci. USA 86, 6925–6929 (1989).
Dreyer, G. B., et al., Proc. Natl. Acad. Sci. USA 82, 968–972 (1985).
Eaton, M. A. W., et al., U.S. Pat. No. 4,719,180, issued Jan. 12, 1988.
Ebright, R. H., et al., Proc. Natl. Acad. Sci. USA 87, 2882–2886 (1990).
Eichhorn, G. L., et al., Biochemistry 10, 2014–2027 (1971).
Emerman, M., et al., EMBO J. 6, 3755–3760 (1987).
Felber, B. K., et al., Proc. Natl. Acad. Sci. USA 86, 1495–1499 (1989).

Fisher, A. G. et al. Nature 320, 367–371 (1986).
Folks, T. M., et al., Science 238, 800–802, (1987).
Frangois, J.-C. et al., Proc. Natl. Acad. Sci. USA 86, 9702–9706 (1989).
Frangois, J.-C. et al., J. Biol. Chem. 264, 5891–5898 (1989).
Frankel, A. D., et al., Cell 55, 1189–1193 (1988).
Galas, D., et al., Nuc.Acid Res. 5:3157–3170 (1981).
Gatignol, A., et al., Proc. Natl. Acad. Sci. USA 86, 7828–7832, (1989).
Gatignol, A., et al., Science 251, 1597–1600, (1991).
Gaynor, R., et al., Proc. Natl. Acad. Sci. USA 86, 4858–4862, (1989).
Gendelman et al., Proc. Natl. Acad. Sci. USA 83, 9759–9763 (1985).
Gorman et al., Proc. Natl. Acad. Sci. USA 79, 6777–6781 (1982).
Green, M., et al., Cell 55, 1179–1188 (1988).
Green, M., et al., Cell 55, 1179–1188, (1988).
Green, M., et al., Cell 58, 215–223, (1989).
Green, M., et al., Cell 58, 215–223 (1989).
Holland, S. M., et al., J. Virol. 64, 5966–5975, (1990).
Htun, H., et al., In Meth. Enzymol. (J. E. Dahlberg and D. M. J. Lilley, eds.); (1991).
Kalebic, T., et al., Proc. Natl. Acad. Sci. USA 88, 986–990, (1991).
Kjems, J., et al., Proc. Natl. Acad. Sci. USA 88, 683–687, (1991).
Kohwi, Y., et al., Proc. Natl. Acad. Sci. USA 85, 3781–3785 (1988).
Lazinski, D., et al., Cell 59, 207–218 (1989).
Lyamichev, V. I., et al., Nucleic Acids Res. 19, 1633–1638, (1991).
Maher, L. J., III, et al., Science 245, 725–730 (1989).
Malim, M. H., et al., Nature 338, 254–257, (1989a).
Malim, M. H., et al., Cell 58, 205–214, (1989b).
Maniatis, T., et al., In *Molecular Cloning: A Laboratory Manual*, Cold Spring Harbor Laboratory (1982).
Marciniak, R. A., et al., Cell 63, 791–802, (1990a).
Marciniak, R. A., et al., Proc. Natl. Acad. Sci. USA 87, 3624–3628, (1990b).
Miller, P. S., et al., U.S. Pat. No. 4,507,433, issued Mar. 26, 1985.
Milligan, J. F., et al., Nucleic Acids Res. 15, 8783–8798 (1987).
Modak, A. S., et al., J. Am. Chem. Soc. 113, 283–291 (1991).
Moser, H. E., et al., Science 238, 645–650, (1987).
Muesing, M. A., et al., Cell 48, 691–701 (1987).
Mullis, K. B., et al., U.S. Pat. No. 4,683,195, issued Jul. 28, 1987.
Mullis, K., U.S. Pat. No. 4,683,202, issued Jul. 28, 1987.
Murakawa, G. J., et al., Nucleic Acids Res. 17, 5361–5375 (1989).
Nabel, G., et al., Nature 326, 711–713 (1987).
Pearson, L., et al., Proc. Natl. Acad. Sci. USA 87, 5079–5083 (1990).
Pei, D., et al., Proc. Natl. Acad. Sci. USA 87, 9858–9862, (1990).
Postel, E. H., et al., Proc. Natl. Acad. Sci. USA 88, 8227–8231, (1991).

Queen, C., et al., Cell 33, 729–734 (1983).

Radding, C. M., et al., PCT International Application, International Application No. PCT/US86/01947, Publication Date Mar. 26, 1987.

Rittner, K., et al., Nucleic Acids Res. 19, 1421–1426, (1991).

Roederer, M., et al., Proc. Natl. Acad. Sci. USA 87, 4884–4888, (1990).

Rosen, C. A., et al., Cell 41, 813–823, (1985).

Roy, S., et al., Genes Dev. 4, 1365–1373 (1990).

Roy, S., et al., J. Virol. 64, 1402–1406, (1990a).

Roy, S., et al., Genes Dev. 4, 1365–1373, (1990b).

Sambrook, J., et al., In *Molecular Cloning: A Laboratory Manual*, Cold Spring Harbor Laboratory Press, Vol. 2 (1989).

Sauer, Robert T., Editor, Methods in Enzymology *Protein/DNA Interactions*, Academic Press (1991).

Sharp, P. A., et al., Cell 59, 229–230 (1989).

Siebenlist, U., et al., Proc. Natl. Acad. Sci. USA 77:122–126 (1980).

Sigman, D. S.,et al., Annu. Rev. Biochem. 59, 207–236 (1990).

Sluka, J. P. et al. Science 238, 1129–1132 (1987).

Soma, et al., Science 244, 1554–1557, (1988).

Southern, P. J., et al., J. Mol. Appl. Genet. 1:327 (1982).

Stahl, S., et al. , J. Mol. Biol. 148:481 (1981).

Strobel, S. A., et al., Science 249, 73–75 (1990).

Takahara, M., et al., J. Biol. Chem. 260(5):2670–2674 (1985).

Tanner, K., Thesis, University of Colorado, Boulder, (1986).

Wang, C. Y., et al., U.S. Pat. No. 4,735,896, issued Apr. 5, 1988.

Wang, C. Y., et al., U.S. Pat. No. 4,879,212, issued Nov. 7, 1989.

Weeks, K. M., et al., Science 249, 1281–1285 (1990).

Weeks, K. M., et al., Cell 66, 577–588 (1991).

Yoshio, T., et al., U.S. Pat. No. 4,849,350, issued Jul. 18, 1989.

Youngquist, R. S., et al., J. Am. Chem. Soc. 109, 7564–7566 (1987).

Zamecnik, P. C., et al., Proc. Natl. Acad. Sci. USA 83, 4143–4146, (1986).

BACKGROUND OF THE INVENTION

Chemical systems for the oxidative cleavage of DNA have been developed and used in recent years (Dervan, 1986; Youngquist et al., 1987; Sluka et al., 1987; Strobel et al., 1990; Chen et al., 1986; Francois et al., 1989; Ebright et al., 1990; Bruice et al., 1991; Sigman et al., 1990; Chen et al., 1987). For example, phenanthroline attached to an oligonucleotide or polypeptide will bind cupric ion and this complex can be used to cleave DNA. In the presence of a reducing agent the bound cupric ion is reduced to cuprous ion, which reduces molecular oxygen to produce hydrogen peroxide. The $H_2O_2$ reacts with the cuprous complex to form a copper-oxo species that is directly responsible for cleavage. Chen et al. (1987) used this approach to convert the *E. coli* trp repressor to a site-specific deoxyribonuclease.

Copper-phenanthrolene has also been tethered to oligonucleotides to induce sequence-specific cleavage of single-stranded and double-stranded DNA (Frangois et al., 1989).

An alternative but chemically analogous system (Dreyer et al., 1985; Dervan, 1986; Moser et al., 1987; Maher et al., 1989) utilizes EDTA-chelated iron tethered to an oligonucleotide to cleave DNA. By attaching an Fe-EDTA group to the DNA-binding domain of the Hin recombinase, Sluka et al. (1987) achieved site-specific DNA cleavage at Hin recombination sites.

In addition to the above chemical systems for the oxidative cleavage of DNA, Corey and Schultz (1987) have converted the nonspecific nuclease staphylococcal nuclease to a site-specific nuclease by attaching it to an oligonucleotide. In this hybrid molecule, the relatively short oligonucleotide is able to confer binding specificity on the target DNA via hybridization (Corey et al., 1987) or triplex formation (Pei et al., 1990).

Although the conversion of DNA-binding molecules to site-specific chemical deoxyribonucleases has been an area of active investigation, efforts to achieve site-specific cleavage of RNA have been mainly limited to the use of ribozymes. Experiments performed in support of the present invention have demonstrated site-specific cleavage of RNA using sequence specific RNA binding proteins.

SUMMARY OF THE INVENTION

The present invention describes a polypeptide having site-specific RNA binding, where the polypeptide is modified to contain a moiety capable of cleaving an RNA backbone, in particular, viral polypeptides having site-specific viral RNA-binding. Exemplary of such polypeptides are the polypeptides presented as SEQ ID NO:1, SEQ ID NO:2, SEQ ID NO:6, SEQ ID NO:7 and SEQ ID NO:22.

A number of cleaving moieties are useful in the practice of the present invention including the following: phenanthroline Cu(II), Zn(II), Fe(II)-EDTA, Cu(II)-bipyridine, and Cu(II)-terpyridine.

In one embodiment of the present invention the RNA-binding polypeptide can be either the HIV TAT or REV proteins, or polypeptides derived therefrom. A preferred embodiment of the present invention is the polypeptide having the sequence presented as SEQ ID NO:1, which further contains an end-terminal cysteine residue, and where the cleaving moiety is phenanthroline Cu(II). Another preferred embodiment is the polypeptide having the sequence presented as SEQ ID NO:2 where the cleaving moiety is phenanthroline Cu(II).

A further embodiment of the polypeptide cleaving reagents of the present invention is the generation of fusion polypeptides containing the RNA-binding polypeptide coding sequence fused in frame to a non-specific nuclease. Alternatively, the non-specific nuclease may be covalently bound to the RNA-binding polypeptide. One preferred embodiment of this aspect of the present invention is the polypeptide having the sequence presented as SEQ ID NO:2 coupled to Staphylococcal non-specific nuclease.

The present invention also includes a method of cleaving a target RNA. The method involves contacting an RNA molecule containing a cognate RNA-binding site with the RNA-binding polypeptide cleaving reagent. Both chemical and nuclease cleaving reagents are useful in this aspect of the present invention.

In one embodiment, the RNA molecule is an HIV RNA and the RNA-binding polypeptide is an HIV-encoded RNA-binding protein, such as TAT, REV, or polypeptides derived therefrom. The RNA-binding polypeptide reagent is supplied at a concentration effective to produce cleavage of the target RNA molecule. Cleavage reactions may further include the addition of a reducing agent, such as mercaptopropionic acid, N-acetyl cysteine, or ascorbate. In one embodiment, for the cleavage of HIV RNA, the cleavage reactions include the addition of the polypeptide reagent, $CuSO_4$ and mecaptopropionic acid. The invention further includes a method of inhibiting expression of viral antigens in infected cells. The method involves exposing the infected cells to the above described polypeptide cleaving reagent where the polypeptide reagent binds, site-specifically, to the RNA target and is able to be taken up by the infected cells. The cells are exposed to a concentration of the polypeptide reagent which is effective to produce reduction in (i) viral antigen expression or (ii) viral transcription in the infected cells. The cells may be exposed to the polypeptide reagent in the presence of a reducing agent, such as N-acetyl cysteine and ascorbate. In one embodiment of the present invention the viral RNA is HIV RNA and the polypeptide reagent is based on the HIV-encoded TAT or REV proteins, or polypeptides derived therefrom. When the polypeptide reagent includes a non-specific nuclease, expression of the polypeptide reagent in infected and/or un-infected cells provides a useful gene therapy to fight viral disease.

In another aspect of the present invention the cleaving agents of the present invention are oligonucleotides having nuclease resistant backbones to which a moiety capable of cleaving RNA backbones has been attached.

BRIEF DESCRIPTION OF THE FIGURES

FIG. 1 illustrates the sequence and structure of a variety of TAR elements.

FIG. 2A presents the primary coding sequence of the HIV-1 TAT protein. This sequence is also presented as SEQ ID NO:1. The region in bold represents the nuclear targeting domain. The underlined polypeptide, a proteolytic product of wild type TAT protein, binds specifically to, TAR-element-containing RNA (Weeks et al., 1990). FIG. 2B presents the sequence of the TAT-derived polypeptide, TAT24C (SEQ ID NO:2), which is derived from the underlined sequence of FIG. 2A. FIG. 2C illustrates a phenanthroline moiety attached to a cysteine residue of a polypeptide.

FIG. 4 presents the sequence of the HIV-1 encoded REV protein. This sequence is also presented as SEQ ID NO:6.

FIG. 5 illustrates the chemistry of the attachment of a phenanthroline moiety to a cysteine-containing polypeptide.

FIG. 6 illustrates the use of 2-iminothiolane for attachment of cleaving moieties to amino groups of polypeptides.

FIG. 11 shows, in bold, potential triplex target sites within the HIV-1-LTR region: A (SEQ ID NO:8), B (SEQ ID NO:9), and C (SEQ ID NO:10).

FIG. 12 shows oligonucleotides [A 1 (SEQ ID NO:11) and 2 (SEQ ID NO:12), B 1 (SEQ ID NO:13) and 2 (SEQ ID NO:14), and C 1 (SEQ ID NO:15) and 2 (SEQ ID NO:16)] designed to target the sequences presented in FIG. 11A, B, and C, respectively. Next to each of these oligonucleotides is the general pattern of base triplets expected when triplexes are formed. Oligonucleotides K (SEQ ID NO:17), L (SEQ ID NO:18), and M (SEQ ID NO:19) are the control oligonucleotides.

FIG. 13 shows a schematic representation of triplex formation at an mRNA target site (bold) using a linear complementary oligonucleotide where the end loop contains basic oligonucleotides (-X-). The RNA sequence is presented as SEQ ID NO:21 and the oligonucleotide is presented as SEQ ID NO:20, where N is an basic residue.

FIG. 14 shows a schematic representation of the HIV-1 REV response element (RRE); this sequence is also presented as SEQ ID NO:23. SEQ ID NO:24 presents the sequence of a truncated RRE binding site which corresponds to Stem II in the figure.

DETAILED DESCRIPTION OF THE INVENTION

I. Selection of RNA-Binding Proteins

Figure 1A:
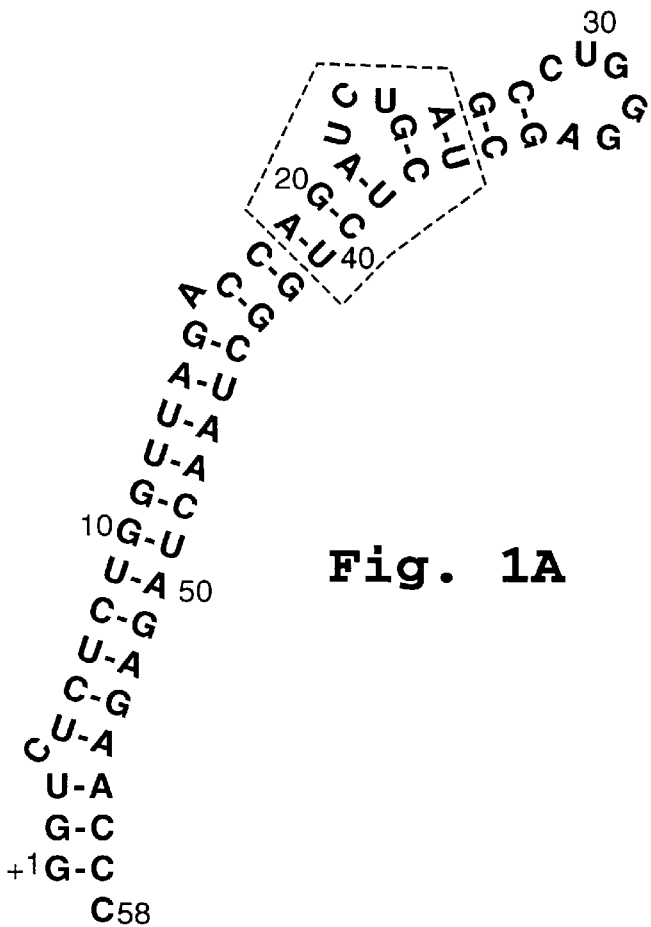
FIG. 1A shows the TAR element of HIV-1 (also presented as SEQ ID NO:3).

Experiments performed in support of the present invention demonstrate that RNA-specific binding proteins can be adapted to perform site-specific cleavage of a target RNA when the target RNA contains the cognate binding site to which the RNA-binding protein binds. One important application of these protein-based cleaving agents is the inactivation of mammalian viruses; in particular, RNA binding proteins modified to accomplish site specific cleavage can be used for inactivating RNA viruses, including the human immunodeficiency viruses (HIV).

Among the criteria for choosing an RNA-binding protein or polypeptide for use in the present invention are the following: RNA target site specific recognition; known or identifiable recognition sequence; the ability to get the protein or polypeptide into cells containing the target RNA; a relatively small protein binding domain is preferable; and fragments containing the protein binding domain should compete well for binding at the RNA target site with the native protein from which they are derived.

Two examples of RNA-binding proteins useful in the practice of the present invention are the TAT and REV proteins encoded by HIV-1. TAT consists of 86 amino acids and is a potent transactivator of long terminal repeat (LTR)-directed viral gene expression and is essential for viral replication (Dayton et al., 1986; Fisher et al., 1986). The amino acid sequence of the TAT protein is presented as SEQ ID NO:1. TAT-induced transactivation requires the presence of the TAR (transactivation response) element, located at the untranslated 5' end of the viral mRNA element.

The RNA sequence of the TAR element is presented as SEQ ID NO:3. The TAR element is capable of forming a stable stem-loop structure (Muesing et al., 1987) in the native viral RNA (FIG. 1). A 3 nucleotide (nt) bulge on the stem of TAR has been demonstrated to be essential for specific and high-affinity binding of the TAT protein to the TAR element (Roy et al., 1990; Cordingley et al., 1990; Dingwall et al., 1989; Weeks et al., 1990). Further, the ability of (i) purified TAT protein and (ii) polypeptide fragments derived from TAT, which contain the nuclear targeting domain, to bind in vitro to RNA containing the TAR element (Roy et al., 1990; Cordingley et al, 1990; Dingwall et al., 1989; Weeks et al., 1990) make TAT a useful model for the RNA-cleaving reagents of the present invention.

In the TAR element, the integrity of the stem and the initial U22 of the bulge (see FIG. 1) are important for TAT protein binding (Roy et al., 1990b). in vivo other sequences that do not affect the binding of the TAT protein to the TAR site are needed for trans-activation of transcription. One such region is the sequence at the loop, which is required for the binding of cellular factors that may interact with the TAT protein to mediate transactivation (Gatignol et al., 1989; Gaynor et al., 1989; Marciniak et al., 1990a; Gatignol et al., 1991).

For the purposes of the present invention, the important components of the protein/RNA interaction are (i) the portion of the protein involved in binding to the specific target sequence, and (ii) the RNA target sequence required for binding. In the case of the TAT protein, both full-length TAT (86 amino acids) and a truncated TAT protein (the N-terminal 72 amino acids) have been expressed as fusion proteins in *Escherichia coli* (Weeks et al., 1990). The TAT proteins were linked to the *E. coli* catabolite activator protein via a protease recognition site. When the fusion proteins were purified and cleaved by the appropriate protease, polypeptide fragments were recovered from each fused protein which resulted from an unexpected cleavage between Gly49 and Arg49 (FIG. 2), at the start of the lysine/arginine-rich RNA-binding region. The fragments resulting from this cleavage, TRF38 and TRF24, comprise the regions extending from Arg49 to residue 86 and Arg49 to residue 72, respectively. Both of these polypeptide fragments specifically bound RNA containing the TAR site (TAR-RNA). Further, a synthetic 14-residue polypeptide spanning the basic region (amino acid residues 48–61 of the TAT protein) bound TAR-RNA as well.

Up to three copies of TRF38 could bind to the wild-type TAR (wt-TAR) site, the first with an apparent dissociation constant of 5 nM and a second copy with an apparent dissociation constant of 20 nM. Only one copy of the TRF38 polypeptide could bind to a truncated version of TAR consisting of the minimal TAT binding site: the minimal site consists of 26 bases containing the upper part of the wt-TAR (FIG. 1C; Muesing et al., 1987). Similar binding characteristics were found for TRF24.

A polypeptide similar to TRF24, designated TAT24C, was chemically synthesized (Example 1A). TAT24C consists of amino acid residues 49–72 of the TAT protein (FIG. 2A) and an additional cysteine residue at the C-terminus (FIG. 2B, SEQ ID NO:2). The TAT24C polypeptide was purified by HPLC and reacted with 5-iodoacetamido-1,10-phenanthroline to attach a 1,10-phenanthroline moiety to the cysteine residue (peptide designated TAT24C-phen, see below).

The above described synthetic polypeptides were then evaluated for TAR-RNA binding. In general, the ability of synthetic polypeptides (both with and without the cleaving moiety) to bind specifically to the target binding site is evaluated using a gel mobility shift assay typically involving two nucleic acid substrates. One substrate contains the wild-type target binding site (e.g., the TAR element of HIV-1 viral mRNA); the other substrate is an RNA that lacks part or all of the recognition sequence and is therefore unable to bind the cognate protein (e.g., a TAR element mutated at the bulge to which TAT is unable to bind, or a tRNA molecule). The second substrate provides a negative control. RNA substrates are prepared as described in Example 2.

Figure 1B:
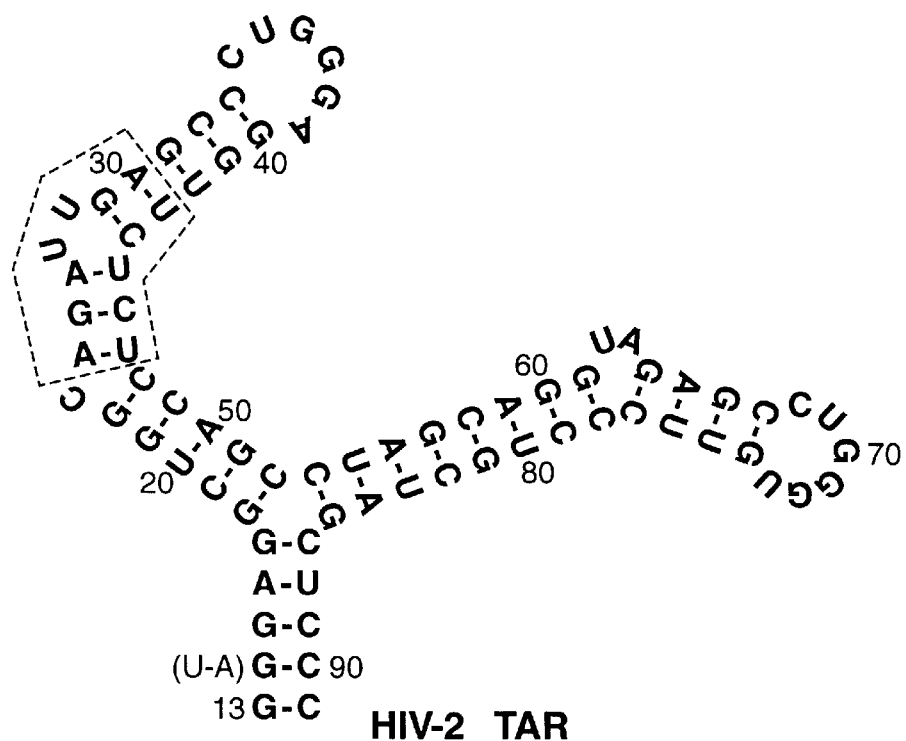
FIG. 1B shows a TAR element of HIV-2 (also presented as SEQ ID NO:4).
Figure 1C:
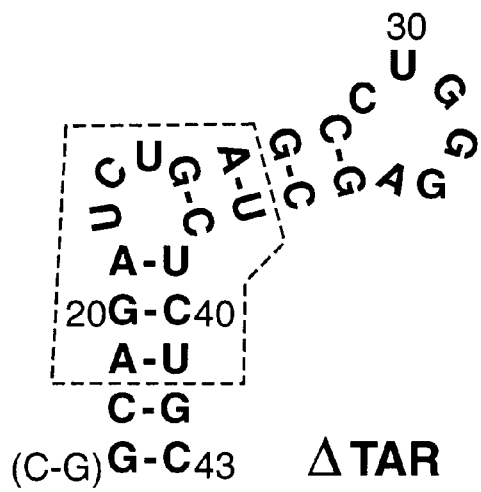
FIG. 1C shows a truncated HIV-1 TAR element designated ΔTAR (also presented as SEQ ID NO:5).
Figure 1D:
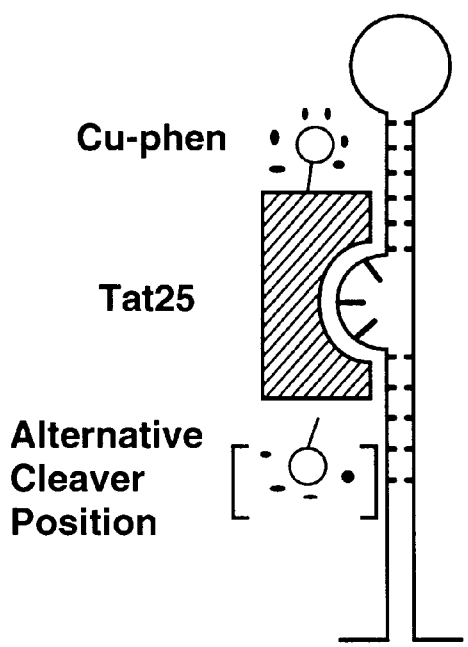
FIG. 1D illustrates the binding of a TAT-peptide, having an attached cleaving moiety, to a TAR element-containing target RNA.

Several TAR-containing RNAs were synthesized to use as substrates in binding assays to test the binding activity of the modified polypeptide TAT24C-phen (Example 2). The predicted secondary structures of the target RNAs are shown in FIG. 1C. The RNA substrate designated HIV-1 TAR is the 57-nt RNA stem-loop structure found in native HIV-1 mRNA (Sharp et al., 1989). The RNA substrate designated ΔTAR is a truncated RNA containing the minimum TAT binding site (nt 17–43) (Weeks et al., 1990). In addition to HIV-1, the etiologically associated virus of AIDS, another retrovirus, termed type 2 (HIV-2) has been reported (Clavel et al., 1986). HIV-2 also possess a functional TAT gene (Arya et al., 1985; Arya and Grallo, 1986). Although the transactivation of genes under the HIV-1 LTR by HIV-2 encoded TAT is quite inefficient, the TAT gene product of HIV-I can effectively transactivate genes under the HIV-2 LTR (Arya et al., 1988; Emerman et al., 1987). Two subelements responsible for the TAT-mediated transactivation in the HIV-2 TAT responsive element (TAR) have been identified and contain two stem-loop structures confined to +1–+103 nucleotides (Arya et al., 1985). The sequence of HIV-2 TAR RNA used in the present study is from +13–90 nucleotides and contains both stem-loop structures.

Figures 3A, 3B, 3C, 3D:
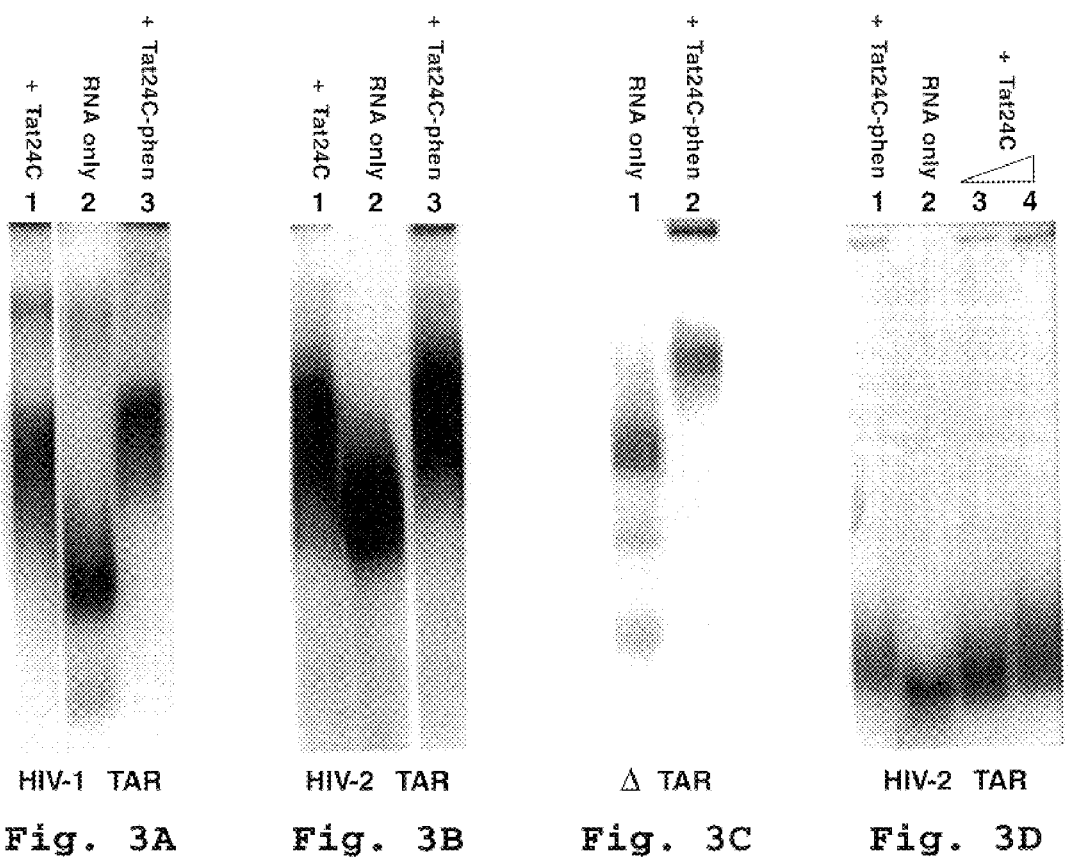
FIGS. 3A–D show the results of gel shift mobility assays using modified and unmodified polypeptides and different RNA substrates.

The above TAT24C polypeptides and RNA substrates were then employed in gel mobility-shift assays (Example 3) to evaluate the binding of the polypeptide to the binding site. FIG. 3 shows a photograph of a representative gel mobility shift assay. In FIG. 3 discrete bands having retarded mobility for samples containing either phenanthroline-modified or un-modified polypeptides demonstrate the binding of both polypeptides to each of the three RNAs containing TAR elements (FIG. 3A–C). The attachment of the extra cysteine and the phenanthroline moiety at the C-terminus of the TAT24 polypeptide does not substantially affect binding to the TAR site. Essentially no retardation of tRNA was observed when it was incubated with high levels of the TAT24C polypeptide (FIG. 3D), indicating relatively specific binding to TAR-site-containing RNA substrates.

The entire TAT protein, as well as fragments of TAT containing the nuclear targeting region, are rapidly taken up by cells. The TAT protein taken up by cells in this fashion specifically activates HIV-1 LTR-linked gene expression (Green et al., 1988; Frankel et al., 1988). The entry of polypeptides containing (i) the nuclear targeting region of TAT and (ii) nucleic acid cleaving agents can be evaluated as described below.

A second HIV protein that is useful in the present invention is the REV protein. REV protein is a regulatory factor essential for viral replication; it is required for the production of viral structural proteins. It appears to exert its effect at the level of splicing and perhaps transport of viral mRNA into the cytoplasm (Malim et al., 1989a, 1989b; Felber et al., 1989); further REV appears to increases the stability of unspliced HIV mRNA (Felber et al., 1989). The REV protein consists of 116 amino acids (FIG. 4, SEQ ID NO:6), encoded by two exons. An arginine-rich domain (residues 38–51) acts as the nuclear targeting domain (Malim et al., 1989b). Mutational analysis has demonstrated that some C-terminal deletion mutants of the REV protein are non-functional, in terms of normal REV functions, but are trans-dominant as illustrated by competitive inhibition of wild-type REV functions.

The action of REV requires the presence of a target sequence termed the REV response element (RRE; FIG. 14, SEQ ID NO:23), located in the HIV envelope gene (Malim et al., 1989a, 1989b). RRE has been mapped to a 234-nucleotide region capable of forming four stem-loop structures and one branched stem-loop structure (Malim et al., 1989a). Footprinting data (Holland et al., 1990; Kjems et al., 1991) suggest that REV binds to six base pairs in one stem structure and to three nucleotides in an adjacent stem-loop structure of the RRE. A 40 nucleotide region in stem-loop II (SEQ ID NO:24) has been implicated as the minimum REV binding region (Cook et al., 1991). Thus, REV offers another potential means of targeting a cleaving agent specifically to HIV RNA and has a potential advantage over the TAT protein in that REV has more potential binding sites.

Other RNA-binding proteins and their cognate binding sites can be characterized as has been described above for the TAT protein and TAR site. Truncated versions of any such protein and/or binding site can be evaluated for protein/-peptide binding using, for example, the gel mobility shift assay or standard filter binding assays (Sauer et al.; Radding et al.). Further, cellular uptake can be evaluated. If the protein is not adequately taken up by cells at concentrations useful to provide intracellular catalytic function, i.e., cleavage, then alternative methods of cellular uptake, such as targeted liposomal delivery where the liposomes carry target cell surface recognition moieties, can be employed to get polypeptide fragments into target cells.

II. Generation of Trans-Acting Proteins Having Cleaving Moieties

A. Chemical Nucleases

A number of chemical moieties are capable of cleaving nucleic acid substrates including phenanthroline (Chen et al., 1986, 1987; Francois et al., 1989; Ebright et al., 1990), Fe(II)-EDTA (Dreyer et al., 1985; Dervan, 1986; Moser et al., 1987; Maher et al., 1989; Sluka et al., 1987), Cu(II)-bipyridine, Cu(II)-terpyridine, and Zn(II) (Modak et al., 1991; Eichhorn et al., 1971; Ikenaga et al., 1974; Breslow et al., 1989). These chemical cleaving moieties can be employed in the present invention as exemplified below with reference to the TAT24 C-phen protein.

Nucleic acid cleaving moieties are attached to the TAT derived polypeptides as described in Example 1B. The chemically synthesized HPLC-purified polypeptides are reacted with 5-iodoacetamido-1,10-phenanthroline (phenanthroline moiety) to obtain polypeptides containing the phenanthroline moiety uniquely attached to the side chain of the cysteine residue. FIG. 5 illustrates the attachment of a phenanthroline moiety to cysteine-containing polypeptides.

The TAT24-C polypeptide (SEQ ID NO:2), consisting of that 24-residue domain plus a single cysteine residue at the C-terminus, was chemically synthesized (Example 1A). A phenanthroline moiety was then attached to the sulfhydryl group of the cysteine to obtain TAT24C-phen (Example 1B).

The cleaving agent can also be attached at residues other than cysteines. For example, phenanthroline can be attached to the side chain-amino groups of lysines and arginines, as well as to the amino group at the N-terminus, by reacting the protein first with 2-iminothiolane hydrochloride, followed by coupling with 5-iodoacetamido-1,10-phenanthroline (Chen et al., 1987). This coupling is illustrated in FIG. 6 and described in Example 1B. Because of the higher loading of cleaving moieties per protein/peptide molecules, such protein/peptide molecules are expected to be efficient reagents for cleavage and are expected to be resistant to in vivo degradation.

Other available nucleic acid cleaving agents can also be used in the methods of the present invention, including Fe(II)-EDTA, Cu(II)-bipyridine, and Cu(II)-terpyridine. If the intracellular reduction potential is not sufficient to recycle metal atoms to its reduced state, the intracellular reduction potential can be affected using N-acetyl cysteine, which increases the intracellular glutathione level (Roederer et al., 1990; Kalebic et al., 1991), in order to assist in keeping the metal atom of the cleaving agent in the reduced state.

Figure 7:
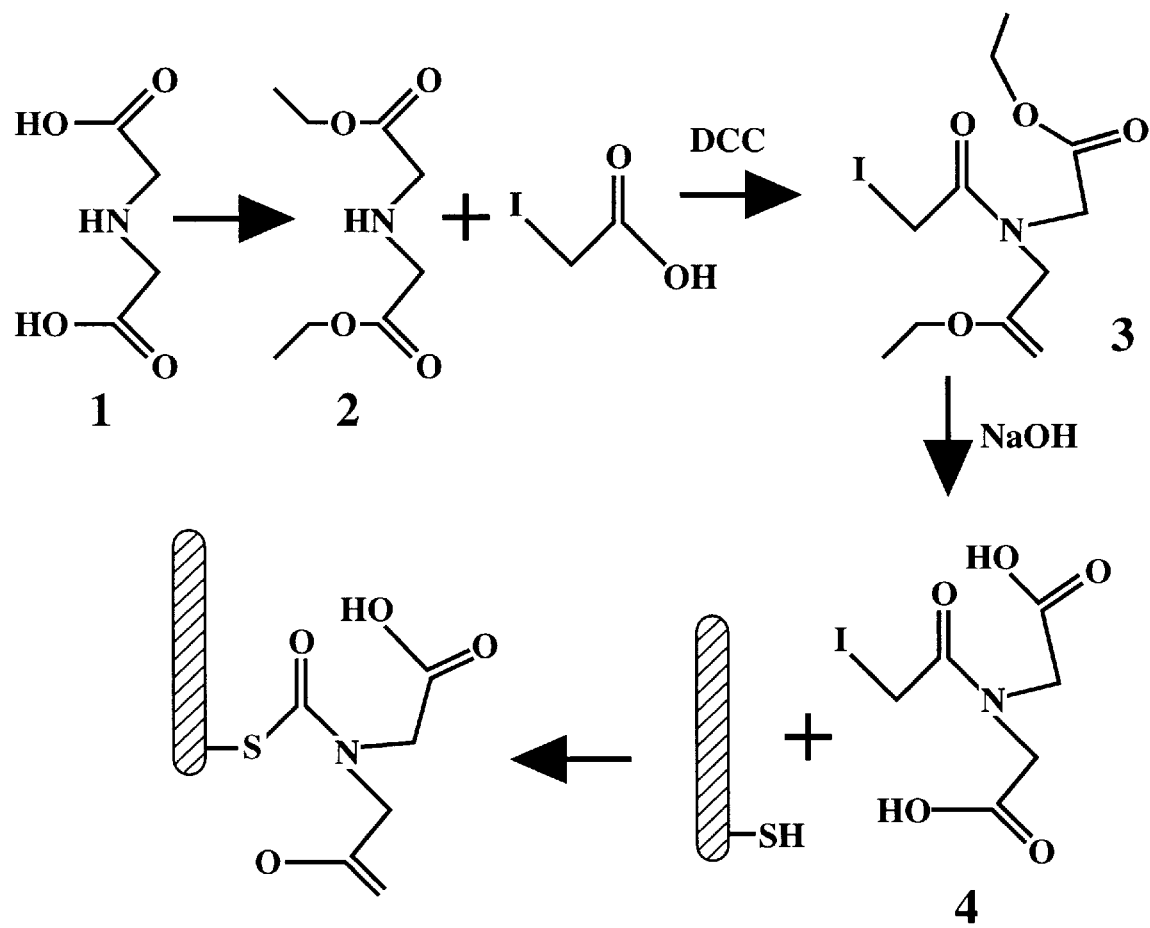
FIG. 7 shows one scheme for attachment of iminodiacetic acid to polypeptides for Zn(II) binding.

Alternatively, different chemical cleaving mechanisms are available. RNA degradation is known to be induced by divalent metal ions, especially Zn(II), in the absence of a reducing agent. The reduced hydrolytic cleavage compared to reaction in the presence of a reducing agent can be at least partly offset by having more than one chelating molecule attached to the polypeptide. One technique for tethering Zn(II) to a protein is via coordination by iminodiacetic acid (Aldrich, Milwaukee Wis.): one possible scheme for such attachment is shown in FIG. 7. Briefly, iminodiacetic acid is converted to its diethyl ester to protect carboxylic functionalities. The resulting product is condensed with iodoacetic acid in the presence of dicyclohexyl carbodiimide (DCC) to obtain compound 3 (FIG. 7). Compound 3 is then reacted with, for example, a polypeptide containing a cysteine residue.

The ability of proteins/peptides, with and without the nucleic acid cleaving moiety, to bind their cognate nucleic acid substrate is evaluated as described above.

Once the polypeptides are screened for specific binding to their cognate nucleic acid binding site, the polypeptides carrying nucleic acid cleaving moieties are next evaluated for their ability to cleave the target nucleic acid.

B. Hybrid-Protein Nucleases

In addition to the above chemical cleaving moieties, a non-specific enzymatic nuclease can be attached to a sequence specific RNA binding protein to form a sequence-specific ribonuclease. Staphylococcal nuclease, a non-specific nuclease that attacks both RNA and DNA, has been converted to site-specific DNA endonuclease by attaching the protein to an oligonucleotide (Corey et al., 1987; Pei et al., 1990).

For the present invention, hybrid fusion proteins are generated between the RNA sequence-specific protein and the coding sequence of Staphylococcal nuclease. The hybrid proteins can be expressed using any number of standard expression systems (e.g., "CLONTECH" commercially available vectors). Typically, the hybrid protein is expressed in *E. coli* using the OmpA-derived expression system (plasmid pONF1) already adopted for the secretion of staphylococcal nuclease (Takahara et al., 1985). In this construct, the signal peptide required for the secretion of ompA protein is fused to the nuclease gene to obtain large amounts of secreted nuclease: the nuclease is then released from the signal polypeptide by appropriate processing. DNA sequences encoding the TAT, REV, or derivative RNA-binding polypeptides are cloned adjacent to and in-frame with the staphylococcal nuclease gene in plasmid pONF1.

The RNA-binding protein coding sequence can be generated by any number of methods including polymerase chain reaction amplification (Mullis et al.; Mullis) and standard cloning technology (Ausubel et al.; Maniatis et al.; Sambrook, et al.). The insertion of the RNA-binding protein/peptide coding sequence is performed by standard cloning methods (Ausubel et al.; Maniatis et al.; Sambrook, et al.). The resulting hybrid proteins are then expressed in *E. coli* and purified (Takahara et al., 1985).

The ability of hybrid proteins/peptide nucleases to bind their cognate nucleic acid substrate is evaluated as described above using, for example, the gel mobility shift or filter binding assays.

Once the hybrid protein/peptide nucleases are screened for specific binding to their cognate nucleic acid binding site, they are next evaluated for their ability to cleave the target nucleic acid.

III. Targeted Cleavage of Nucleic Acids

The chemical nuclease activity of Cu(II)-complexed 1,10-phenanthroline derives from an oxidative attack on the sugar ring by a copper-oxo species generated in the presence of a reducing agent (Sigman et al., 1990).

Figure 8A:
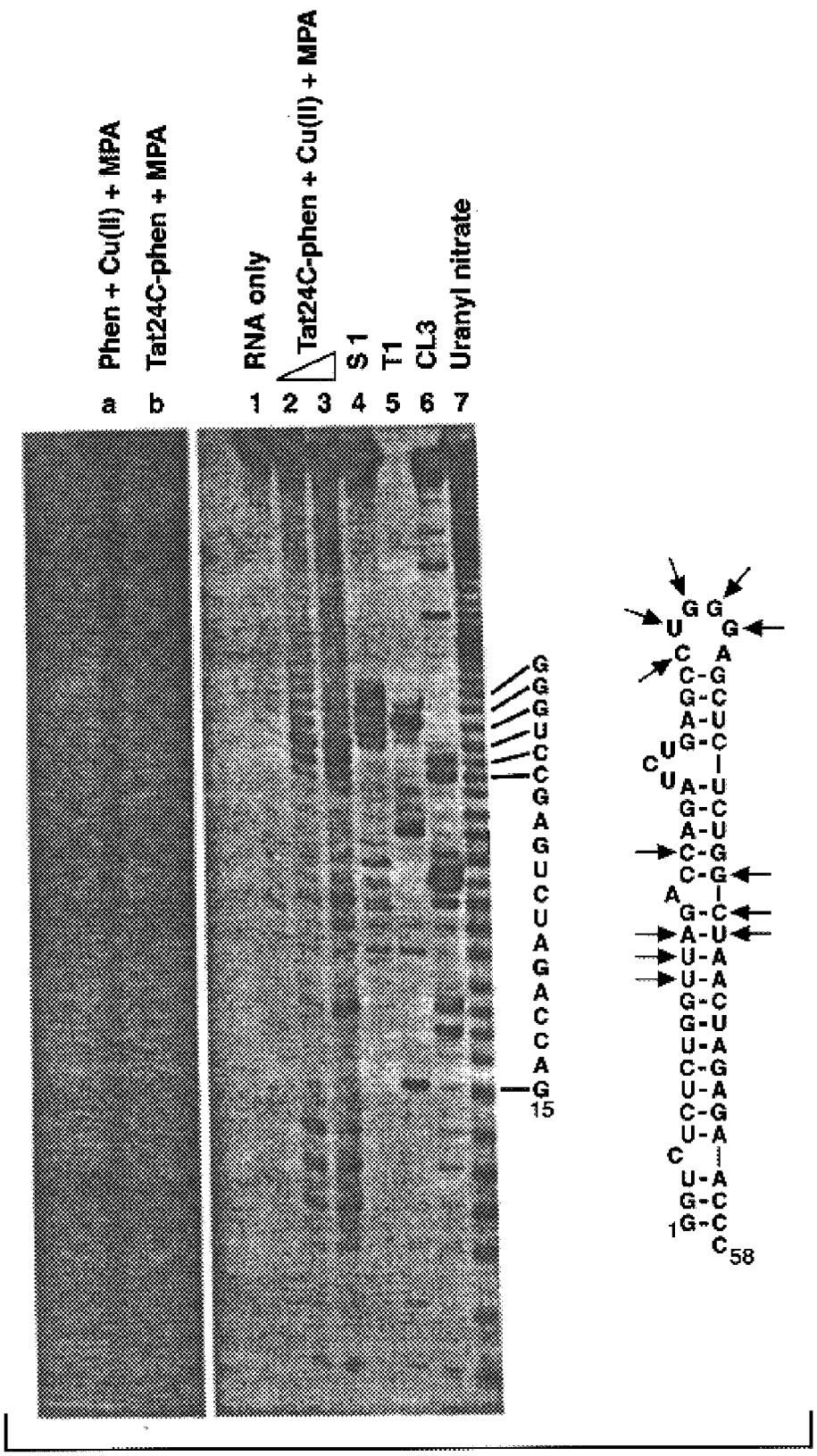
FIGS. 8A and 8B show the results of cleavage assays using a variety of cleaving agents and an HIV-1 TAR-element containing substrate. The drawing of the RNA substrate indicates cleavage sites (arrows) of TAT-based cleaving agents.
Figure 8B:
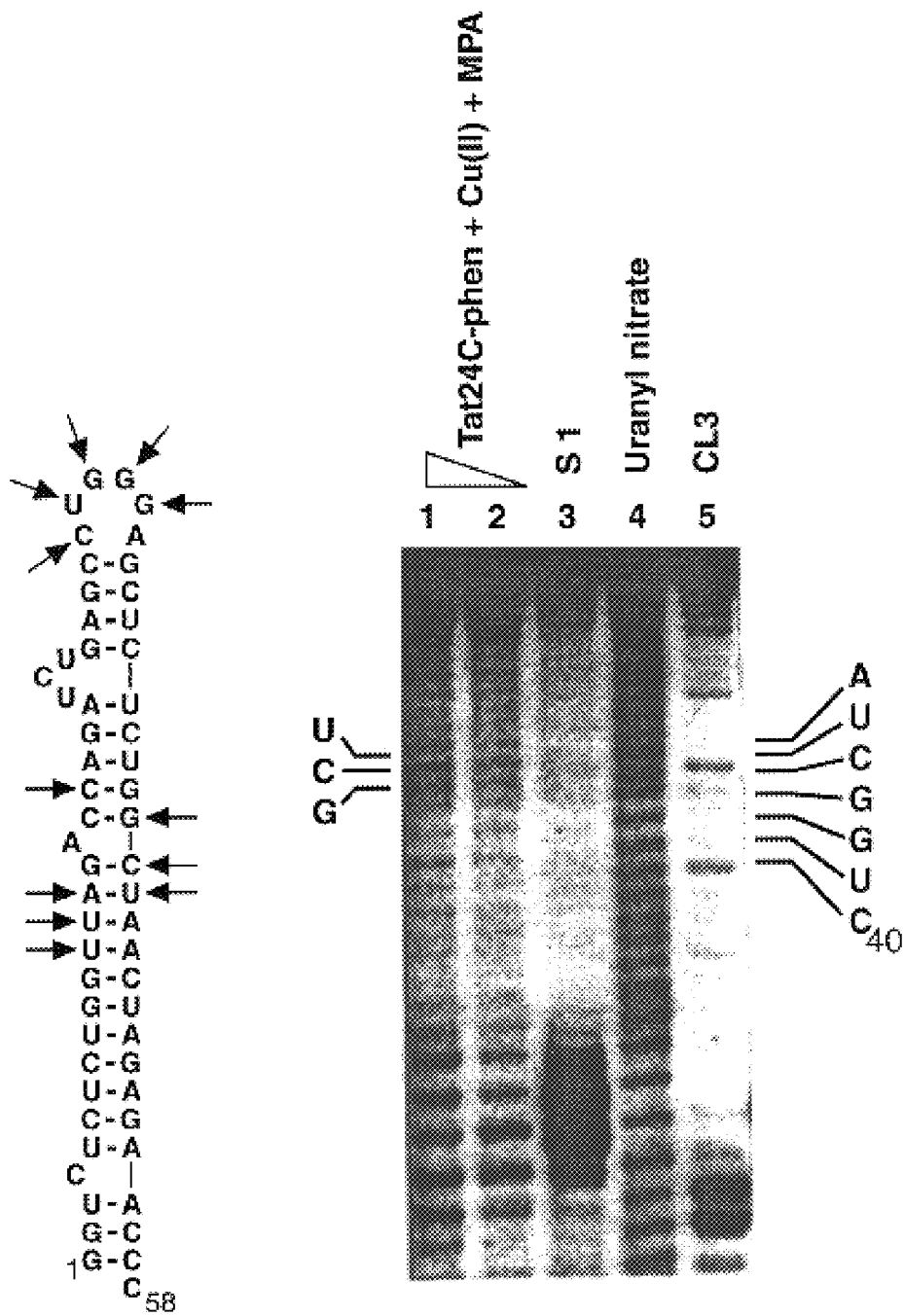

The above described polypeptides were tested for their ability to cleave RNA substrates which contained cognate binding sites. Typically, RNA target molecules containing the binding sites were 5'-end-labeled, purified on denaturing polyacrylamide gels, and annealed for use as substrates for cleavage (Example 2). A typical cleavage reaction contained $10^3$ cpm of end-labeled RNA and 40–100 ng of polypeptide. Example 4A describes RNA cleavage reactions utilizing the TAT24C-phen polypeptide. The target RNA was incubated with TAT24C-phen at 25° C. for 10 min before the cleavage was initiated by adding $CuSO_4$ and mercaptopropionic acid. After incubating for a given period of time, the reaction was stopped by the addition of 2,9-dimethyl-1,10-phenanthroline. RNAs were then isolated and analyzed on denaturing 15% sequencing gels. The results of this cleavage reaction, when HIV-1 TAR was used as the substrate, are shown in FIG. 8A and FIG. 8B. As seen in lanes 2 and 3 (FIG. 8A), there is a specific cleavage occurring primarily at the beginning of the loop of the target stem and loop structure (FIG. 1). This is an expected site of cleavage based on binding of the polypeptide at the three-nucleotide bulge. A possible secondary cleavage site may be due to flexibility of the phenothroline-containing protein of the polypeptide, allowing it to reach to stem on the other side of the binding site.

Since Cu(II)-phenanthroline is known to be biased in favor of cleaving unpaired bases of RNA (Murakawa et al., 1989), HIV-1 TAR was incubated with 1,10-phenanthroline-Cu(II) as a control and the cleavage pattern induced by free phenanthroline is shown in lane a (FIG. 8A). As expected, free phenanthroline cleaves nonspecifically, however, the unpaired bases at the loop and the bulge are somewhat hyperreactive. The reactivity of loop nucleotides towards free phenanthroline-Cu(II) is different from their reactivity toward the polypeptide.

Figure 8C:
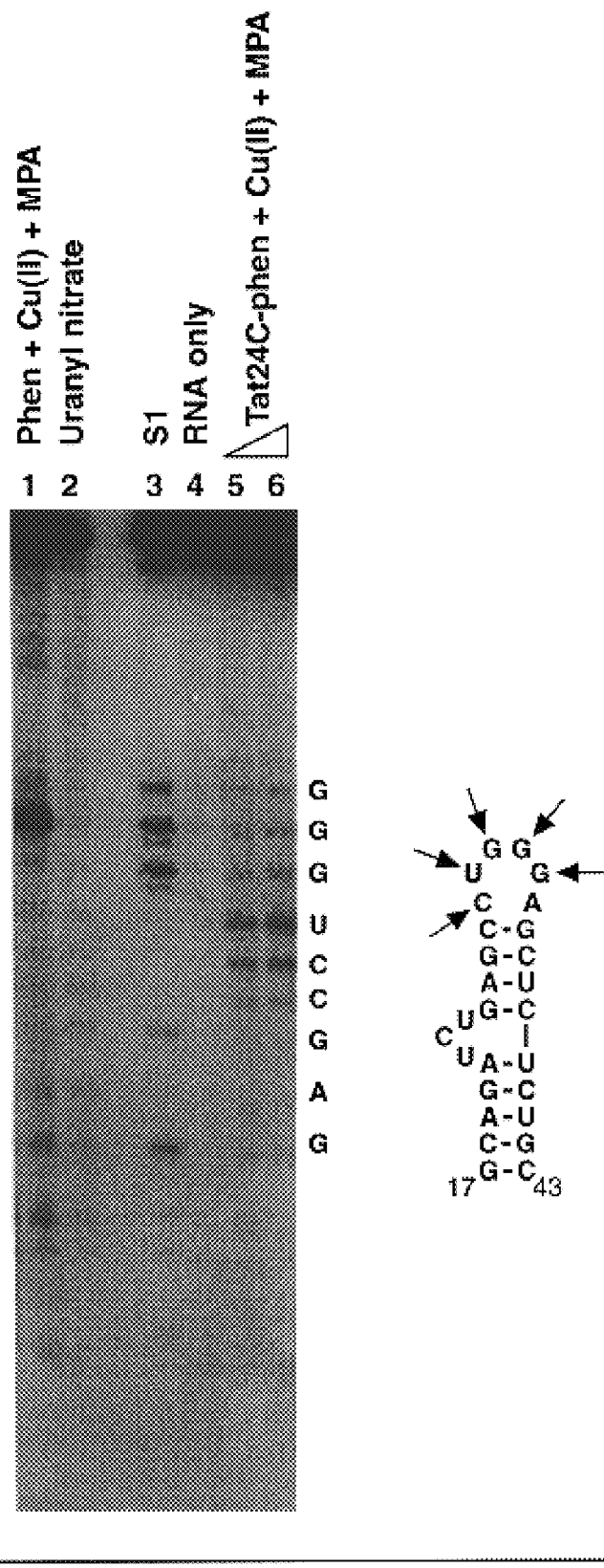
FIG. 8C shows the results of cleavage assays using a variety of cleaving agents and a truncated HIV-1 TAR-element-containing substrate. The drawing of the RNA substrate indicates cleavage sites (arrows) of TAT-based cleaving agents.

The cleavage induced by TAT24C-phen on the ΔTAR sequence is illustrated in FIG. 8C (Example 4B). The cleavage pattern of this truncated substrate is consistent with the cleavage pattern observed for the full-length TAR. With ΔTAR, the cleavage is restricted to the loop. The reactivity of nucleotides occupying the loop towards the polypeptide is different from that of free phenanthroline (compare lane 1 with lanes 5 and 6, FIG. 8C).

Figure 9A:
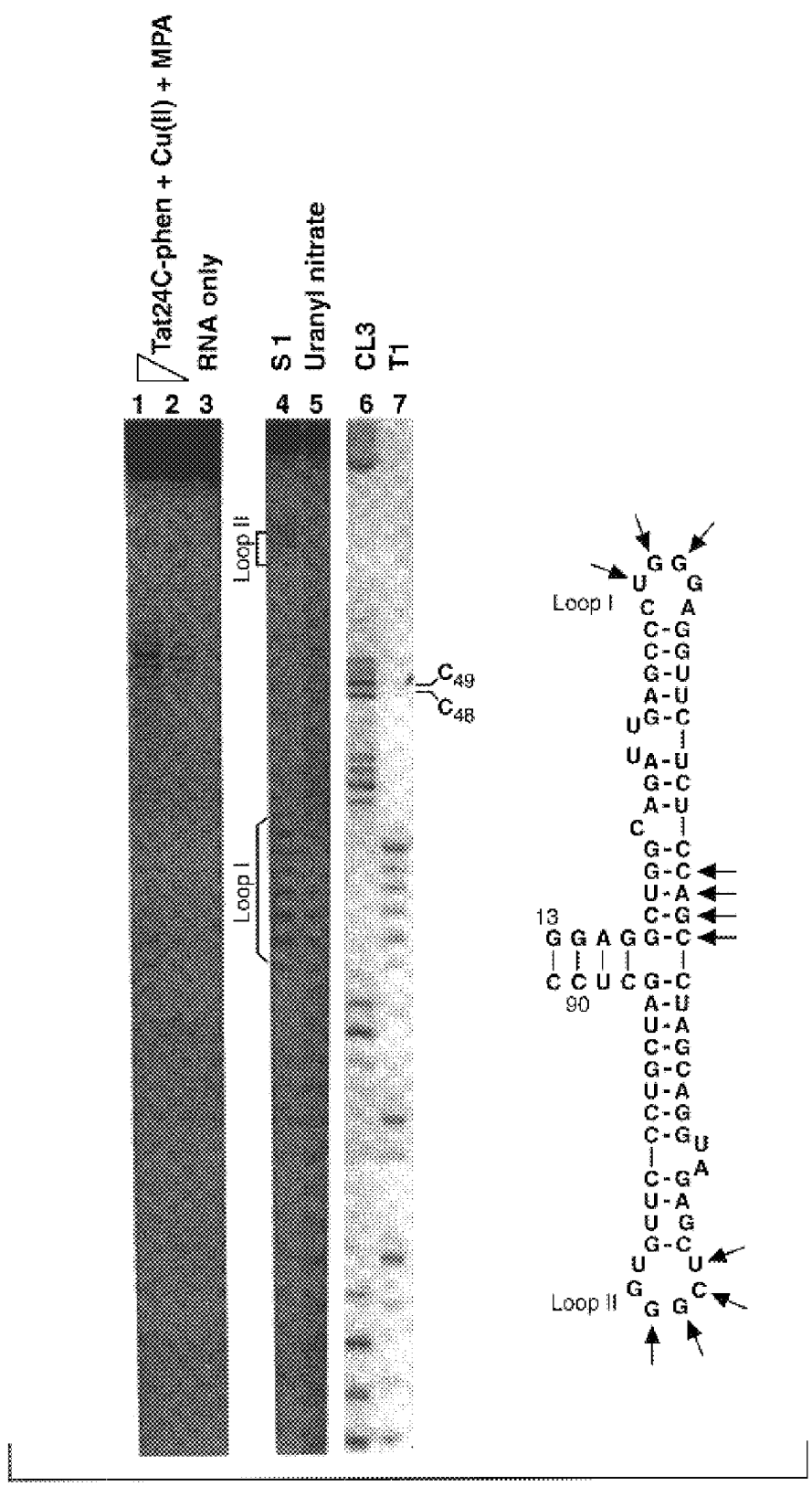
FIG. 9A shows the results of cleavage assays using a variety of cleaving agents and an HIV-2 TAR-element containing substrate. The drawing of the RNA substrate indicates cleavage sites (arrows) of TAT-based cleaving agents.

The effect of the TAT24C-phen was examined relative to the HIV-2 TAR site (Example 4C). The primary cleavage site found on the HIV-2 TAR is somewhat unexpected (FIG. 9, lanes 1 and 2). Based on the results observed with the HIV-1 TAR substrates, the cleavage site of the HIV-2 target was anticipated to be predominantly at the loop close to the TAT binding site (loop 1, FIG. 9A). However, the TAT24C-phen polypeptide appears to cleave the HIV-2 TAR-RNA at a site located towards the 5' end of its binding site (FIG. 9A). Unlike the HIV-1 TAR RNA and Δ TAR RNA substrates, the primary cleavage site in the HIV-2 TAR site is not in the loop and does not appear to have unpaired bases (as implied by the S1 nuclease cleavage reactions the results of which are shown in lane 4, FIG. 9A).

The primary site of cleavage in the HIV-2 substrate is likely the consequence of the tertiary structure of the HIV-2 TAR RNA. Unlike HIV-1 TAR RNA sequence which has a single stem-loop, the HIV-2 target consists of two stem-loop structures: the HIV-2 TAR RNA sequence may have a complex tertiary structure reduces the otherwise favorable interaction of the polypeptide-bound cleaving moiety with the loop. The TAT24C-phen polypeptide does, however, cleave both HIV-2 target loops. The cleavage of the loop 1 is expected and the cleavage of the remote second loop may be the result of the two loops being in a spatially close orientation within the overall secondary structure of the HIV-2 substrate.

Overall, the cleavage sites of the RNA targets lie on either side of the bulge where the TAT protein is known to bind (Roy et al., 1990; Cordingley, et al., 1990; Dingwall et al., 1989; Weeks et al., 1990). As shown in FIGS. 8A and 8C, lane a and lane 1, respectively, free phenanthroline moieties cleave relatively randomly, but the unpaired bases at the loop (especially $G_{32}$) and the bulge are most reactive. This is consistent with previous work which showed that Cu(II)-phenanthroline preferentially cleaves unpaired bases of RNA (Murakawa et al., 1989). In view of this result, the above experiments performed in support of the present invention indicated that tethering phenanthroline to the TAT24C polypeptide suppresses non-specific cleavage on TAR RNA. In the absence of cupric ions, TAT24C-phen produces no cleavage (FIG. 8A, lane b).

The cleavage pattern on ΔTAR, which lacks the base of the stem, is consistent with that of full-length TAR (FIG. 8C), suggesting that the minimum TAT binding site is sufficient to be recognized by the TAT24C-phen polypeptide. On ΔTAR, the cleavage is restricted to the loop, but the pattern is very different from that for cleavage by free phenanthroline (FIG. 8C, compare lane 1 with lanes 5 and 6).

In contrast to cleavage of HIV-1 TAR, for which the primary site is at the loop adjacent to the TAT binding site, cleavage of HIV-2 TAR takes place mainly at the stem, roughly midway between the two loops (FIG. 9A, lanes 1 and 2). HIV-2 TAR has two 2-nt bulges, both of which have the consensus TAT binding motif (Weeks et al., 1990; Green et al., 1988; Frankel et al., 1988; Milligan et al., 1987; Arya et al., 1988; Weeks et al., 1991; Murakawa et al., 1989).

When tRNA was used as the substrate for cleavage, the cleavage pattern induced by TAT24C-phen was identical with that caused by free Cu(II)-phenanthroline (FIG. 9B), indicating that TAT24C-phen does not induce site-specific cleavage on RNA lacking a TAR site.

In the absence of the reducing agent mercaptopropionic acid, Cu(II)-complexed TAT24C-phen still cleaves TAR-containing RNA. When mercaptopropionic acid was replaced by ascorbic acid, a reducing agent more suitable for in vivo studies, the rate of cleavage increased.

Experiments performed in support of the present invention which demonstrate the specific cleavage induced by TAT24C-phen on TAR-containing RNAs, taken in combination with previous reports that some mutations of the TAT protein are transdominant (Green et al., 1989; Pearson et al., 1990) support the potential efficacy of using the TAT-24C-phen polypeptide for the inactivation of HIV RNA even in the presence of native TAT, as would be found inside an HIV-infected cell.

The above described method can be applied to test the cleavage of a number of RNA target molecules using modified binding polypeptides, i.e., proteins known to have binding sites in a selected RNA target molecule. For example, REV-derived polypeptides encompassing the nuclear targeting domain (underlined sequence, FIG. 4) are synthesized and attached to cleaving agents as described for reagents based on the TAT protein. A synthetic peptide spanning the basic domain of the REV protein (SEQ ID NO:22) has been shown to bind specifically to the RRE target (Kjems et al., 1991); in vitro the same peptide inhibits the splicing of mRNA containing RRE.

Alternatively, as described above, target RNA molecules can be cleaved using polypeptides modified with iminodiacetic acid in the presence of $ZnCl_2$.

The efficiency of cleavage reactions using any RNA binding proteins or polypeptides, which are derived from these proteins, depends on several factors: (a) the binding affinity and specificity of the reagent; (b) the spatial positioning of the cleaving moiety; (c) the nature of the cleaving reagent; and (d) reaction conditions.

First, if a binding protein is to be used as a truncated reagent, the specificity and the binding affinity of a binding polypeptide to its cognate binding site in an RNA target molecule may potentially be increased by increasing the length of the polypeptide, for example: (i) by extending the polypeptide length from the N-terminus, (ii) the C-terminus, or (iii) both ends of the basic nuclear targeting domain of a transactivator.

In the case of the TAT and REV proteins the maximum number of residues needed to maximize specific binding is not expected to be more than 50 residues, because both trans-activators are relatively small, on the order of 100 residues, and both have functional domains besides the RNA binding domain. Two other approaches to increasing the binding specificity of TAT24C-phen to the target TAR site are as follows: (i) evaluating in vitro generated mutations (Ausubel et al.) for mutations that increase the binding specificity of the protein/peptide to the cognate binding site (Sauer et al.); (ii) chemical alterations of the polypeptides which can effect a general improvement of RNA binding, such as replacing Asp and Glu with Asn and Gln. Alternatively, chemical modification can be used to convert Asp and Glu to esters or amides to increase the net positive charge of the polypeptide. Chemical modification reactions that occur in solution can be performed on the polypeptide bound to the target RNA where possible, so that sites critical for binding are protected against alteration (Galas et al.; Siebenlist et al.).

Second, in order to improve the binding of a protein or polypeptide to its cognate RNA binding site the spatial positioning of the cleaving moiety may be adjusted. Because of the three-dimensional folding of polypeptides, the position of the cleaving agent within the polypeptide molecule can be crucial for the cleavage. In the cases of TAT and REV proteins the three dimensional structure of the proteins is not known. Accordingly, favorable locations for the placement of the cleaving moiety can be empirically determined; the single cysteine residue can be placed at several positions, including the N-terminus, C-terminus, and internal positions of the polypeptide which do not affect RNA-binding ability.

Third, in order to improve the efficiency of cleavage reactions using RNA binding proteins or polypeptides derived from these proteins the nature of the cleaving reagent can be modified as described above, using chemical or enzymatic cleaving moieties.

Lastly, reaction conditions can be modified to improve cleavage of RNA substrates by, for example, increasing reduction potential in the reaction mixture or intracellularly by, for example, adding N-acetyl cysteine (or perhaps ascorbate) to the system. In vitro reaction conditions can also be modified by altering temperature, ionic conditions, the amount and type of reducing agent, and pH.

The cleavage assay will be used to assess the effects of the above factors on the efficiency of the cleavage reaction. Single variables will be modified to evaluate efficacy. For example, to assess the cleavage induced by different peptides, an identical concentration of the different peptides are used in reaction mixtures containing the other reagents at fixed concentrations. After the cleavage reaction has been carried out for a specified period, digested end-labeled RNAs (e.g., HIV-1 TAR) will be resolved on sequencing gels, the gels will be autoradiographed, and bands corresponding to starting material (intact RNA) and cleavage products will be excised. The radioactive counts present in the excised bands will be determined by scintillation counting. The relative concentrations of cleavage product to starting material is then determined (($cpm_{prod}/cpm_{prod}+cpm_{intact}$)100). Densitometry scanning can also be used to evaluate efficiency of cleavage reactions by using films which have not been overexposed.

IV. Oligonucleotides as Anti-Viral Target Agents

An alternative method to target cleaving agents to RNA targets are oligonucleotides. The chemistry for attaching cleaving groups to DNA fragments in order to sequence-specifically cleave single- and double-stranded DNA targets has been described (Chen et al., 1986; Francois et al., 1989; Dreyer et al., 1985; Dervan, 1986; Moser et al., 1987; Maher et al., 1989). RNA molecules contain both single- and double-stranded regions that can offer targets for oligonucleotide binding (Zamecnik et al., 1986; Rittner et al., 1991). To be effective, RNA oligonucleotide agents must continuously bind to the target molecules in such a way as to inactivate them. However, when a cleavage agent is attached to RNA oligonucleotides, the oligonucleotides only need to bind the target RNA long enough to cleave it in order to achieve permanent inactivation.

In order to generate RNA-binding oligonucleotides which contain cleaving agents, a chosen cleaving group (see above for chemical and enzymatic cleaving groups) is attached to oligonucleotides which are resistant to cleavage by endogenous nucleases. Such backbones include deoxyribose or ribose sugar moieties connected by methyl phosphonate or phosphorothioate linkages (Miller et al., 1985).

Cleaving agents are attached to either end of the oligonucleotide, or, if necessary, to both ends of the molecule to maximize cleavage and minimize exonucleolytic degradation. RNA-binding oligonucleotides have sequences of the following two types: (i) sequences designed to form a duplex with putatively single-stranded regions of a target RNA, and (ii) sequences designed to form triplexes with homopurine regions of the DNA which encodes the RNA-target, for example, a DNA pro-virus.

In the case of the HIV virus, one mRNA target site is the TAR region, because base pairing at this site by a complementary oligonucleotide is expected to block formation of the stem-loop structure required for binding and transactivation by TAT. An inter-molecular duplex is potentially more stable than the intra-molecular stem-loop duplex due to the absence of unpaired bases. Further, such an inter-molecular duplex may be able to displace the stem-loop structure by pairing initially with the loop or with single-stranded regions adjacent to the stem, particularly in view of the observation that alteration of non-essential sequences adjacent to TAR create competing secondary structures which inhibit TAR function (Berkhout et al., 1989).

A major advantage of targeting the DNA pro-virus associated with an RNA virus is that typically only one, or a few copies, of integrated, transcriptionally active DNA are present per cell in contrast to many copies of mRNA which may be present in an infected cell (Soma et al., 1988). Homopurine-homopyrimidine regions of duplex DNA can bind single-stranded oligonucleotides having the same sequence as either the homopurine or the homopyrimidine strand of the target DNA but with the reverse polarity (Dervan, 1986), forming purine-purine-pyrimidine or pyrimidine-purine-pyrimidine triplexes, respectively. The purine-purine-pyrimidine triplexes typically require a divalent cation such as $Mg^{++}$ or $Zn^{++}$ for their stability but are relatively independent of pH (Lyamichev et al., 1991). The pyrimidine-purine-pyrimidine triplexes require divalent cation but are favored by slightly acid pH.

The triple helix approach for targeting DNA to inhibit expression has had limited use due to the requirement for homopurine target sequences. Triplex formation at an oligopurine·oligopyrimidine tract can be induced by a single strand consisting of either only pyrimidines or only purines. Sequence-specific recognition by the oligopyrimidine strand relies on the formation of Py·PuPy (C+·GC and T·AT) base triplets (Moser et al., 1987). In this case, the oligopyrimidine strand is parallel to the purine tract of the duplex. An oligopurine strand, on the other hand, lies anti-parallel to the purine tract of the duplex, and sequence-specific recognition in this case is brought about by Pu·PuPy (G·GC and A·AT) base triplets (Kohwi et al., 1988; Beal et al., 1991). A sequence of 15–18 purines is required to achieve sufficient specificity, and this requirement limits the triplex approach in controlling the expression of a particular gene. Although long homopurine stretches do occur in viral genomes, finding such a sequence within a gene vital to the virus can be difficult.

Experiments performed in support of the present invention support that triplex formation can occur at tandem oligopurine·oligopyrimidine sequences using normal DNA, without any unnatural linkages or synthetic base analogues. Briefly, such sequences utilize both types of base triplets, Pu·PuPy and Py·PuPy, in forming a triplex. In other words, this approach allows the formation of triplexes at base sequences made up of both purines and pyrimidines. In addition, the incorporation of Pu·PuPy base triplets has the advantage that triplex formation does not demand low pH, which is usually the case when the C+·GC base triplet is involved.

For use in the present invention, triplex-forming oligonucleotides are designed to interact with homopurine-homopyrimidine sequences in the pro-virus. For example, within the HIV-1-LTR region are three potential targeting sites (sequences in bold, FIG. 11A, 11B, 11C) for targeting with single-stranded oligonucleotides. These cleaving-oligonucleotide reagents bind and cleave the DNA provirus as well as the mRNA of HIV, increasing the likelihood of preventing viral replication.

All three target sites are located in the control region of the HIV-LTR (i.e., upstream of the transcription initiation site) and therefore do not interact with mRNA sequences to function as anti-sense mediators. The potential target sites A, B, and C have different triplex forming motifs:

(i) Site A, consisting exclusively of purines, is targeted for triplex formation using oligonucleotides A-1 and A-2 (FIG. 12), which are capable of forming triplexes with Pu·PuPy and Py·PuPy base triplets, respectively.

(ii) Site B consists of a tract of pyrimidine residues flanked by two purine tracts and is targeted with oligonucleotides B-1 and B-2 (FIG. 12), having the correct polarity to bind with two strands of the target (see above).

(iii) Site C has some pyrimidines scattered within a highly purine-rich sequence, and oligonucleotides C-1 and C-2 (FIG. 12) are directed toward site C.

In FIG. 12 oligonucleotides K, L, and M, correspond, respectively, to sites A, B, and C in the reverse polarity and are therefore blocked from triplex formation; these oligonucleotides are used as controls. Test oligomers with and without phenanthroline are used to assess the effect of cleavage.

Attachment of 1,10-phenanthroline to oligonucleotides is achieved as follows. During chemical synthesis each oligonucleotide is synthesized with a thiol group at the 5' end by use of the "C6-thiol modifierd™" reagent from Clontech (Palo Alto, Calif.) according to the manufacturers instructions. The oligonucleotides are de-protected with $NH_4OH$ and treated with silver nitrate to expose the thiol group. The oligonucleotide is immediately reacted with 5-iodoacetamido 1,10-phenanthroline as described above to covalently link 1,10-phenanthroline to polypeptides.

In vitro triplex formation by the oligonucleotides at their designated target sites is assayed by determining site-specific cleavage induced at the target sequences by the test oligonucleotides equipped with the phenanthroline moiety.

pHIV-1LTR-CAT is linearized with HindIII, end-labeled with $^{32}P$-γ-ATP using polynucleotide kinase, and subjected to a second restriction digest to obtain a uniquely labeled DNA fragment containing the duplex target sequence. After gel purification, this DNA fragment is mixed with an appropriate modified oligonucleotide in a buffer containing 10 mM Tris-HCl, 100 mM NaCl, 100 μM spermine, and 10 mM $MgCl_2$. The pH of the buffer is adjusted depending on the sequence of the target (a lower pH is used for the formation of C+·GC base triplets).

After incubation at 20° C. for 30 min., cleavage is initiated by adding $CuSo_4$ (to 10 μM) and mercaptopropionic acid (to 2.5 mM). Cleavage products are resolved on sequencing gels along with the products of sequencing reactions. This method allows the mapping of the site of triplex formation and the cleavage efficiency (detected by counting the radioactivity of excised gel bands); cleavage efficiency is used to quantitate the efficiency of triplex formation.

To evaluate in vivo triplex formation the CAT gene is transiently expressed under the direction of HIV-1 LTR in HeLa cells. HeLa cells are transfected with pHIV-1LTR-CAT, using the DEAE-dextran technique (Queen et al., 1983). Twelve hours after transfection, the cells are incubated with an oligonucleotide, as described by Postel et al.

(1991), and mitomycin C (SIGMA) is added to the medium to induce CAT expression. Cells are harvested at 12 and 24 hr and CAT activities determined as described by Gorman et al. (1982) and compared to controls, i.e., cells that have been exposed to control oligonucleotides (K, L, and M) and cells without oligonucleotide treatment.

To assess the effect of target sequence cleavage, oligonucleotides carrying phenanthroline are complexed with $CuSO_4$ before being introduced to the cell medium. Ascorbic acid (or mercaptopropionic acid) is supplied to the medium 12 hr after the oligonucleotide treatment and cells are harvested and assayed for CAT activity after another 24 hr.

The effect of oligonucleotides in the presence of TAT protein is assayed using p-HIV-1LTR-CAT under stable expression conditions (described above). CAT-active clones are transfected with a TAT expression vector and these cells, which are transiently expressing TAT are used for oligonucleotide treatment followed by the measurement of CAT activity.

Figures 10, 11A, 11B, 11C:
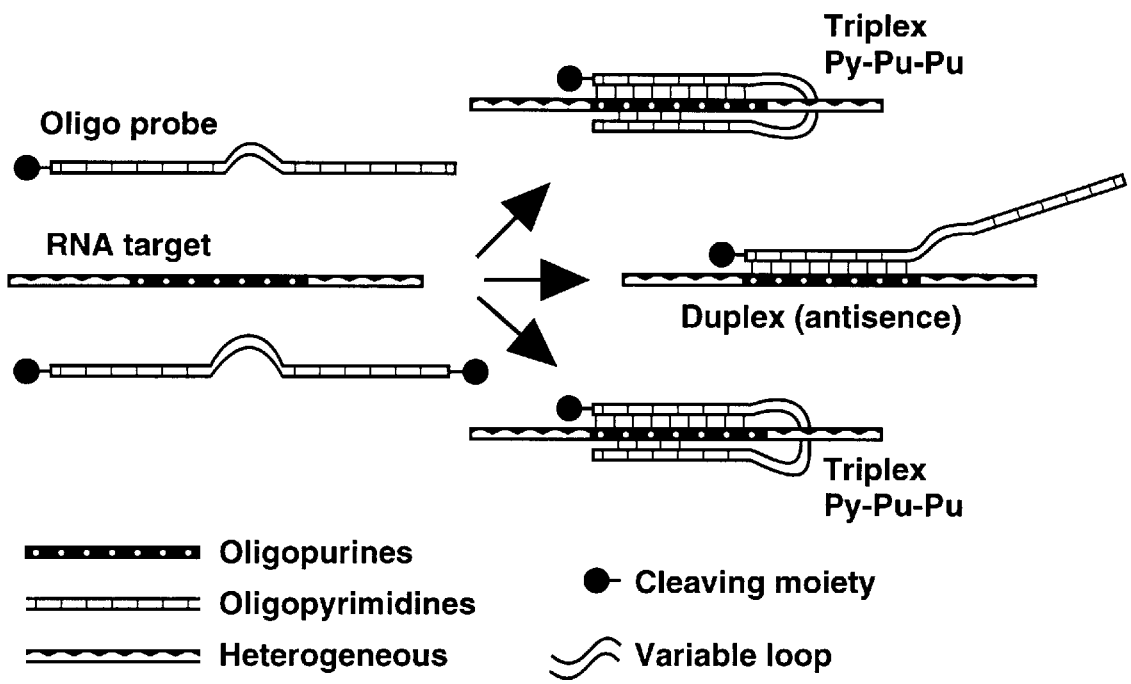
FIG. 10 provides an overview of a method for targeting and inactivation of HIV mRNA using oligonucleotides which contain cleaving moieties.

An alternative to the above described triplex helix methods is to use an oligonucleotide-based approach where a single-stranded oligonucleotide is capable of forming a triplex with HIV mRNA by contributing two "strands" connected by a hairpin loop (FIG. 10; FIG. 13). This triplex-directed anti-sense approach is expected to be more effective in arresting biological processes such as translation and reverse transcription than is the convention anti-sense approach where a DNA-RNA duplex is formed. Triplex formation in this fashion is highly selective and of high affinity and may not be a substrate for enzymes such as helicases. The action of such helicases has been a potential problem in the conventional anti-sense approach (Bass et al., 1987).

For cleavage of target RNA substrates, oligonucleotides have a chemical cleaving group attached to one end (FIG. 10) and an intercalator linked to the other end. Because de-protection procedures are different and independent from each other, derivatization at the two ends can be performed at two stages of oligonucleotide synthesis.

V. Utility

The cleaving reagents of the present invention provide means for a method of cleaving RNA targets at specific sites. Such cleavage is useful for the analysis of RNA structure and function as well as diagnostic analyses. One example of a diagnostic application is to isolate RNA from a cell infected with a particular RNA virus. Total or poly-A+ RNA (Ausubel et al.) is end labeled. The RNA is then isolated away from free label and the amount of incorporated label estimated, for example, by scintillation counting. The labeled RNA is then treated with an RNA cleaving agent, such as an RNA-binding protein combined with a chemical cleaving moiety, and the amount of liberated label is used as an indicator of the concentration of RNA contain the RNA-binding protein cognate binding site. The cleaving reagents of the present invention are particularly desirable for use with RNA virus targets or their pro-viral DNA forms: for example, cleaving HIV genomic RNA or pro-viral DNA.

The cleaving reagents of the present invention are also useful in a method of inhibiting expression of RNA. viral (e.g., HIV) antigens in cells infected with the virus. For this application, the infected cells are exposed to an RNA binding protein or polypeptide modified to contain a cleaving moiety (i.e., the reagent), at a reagent concentration effective to produce reduction in viral antigen expression in the infected cells. Examples of such reagents for anti-HIV agents have been described above.

It has been demonstrated that chemically synthesized full-length TAT protein as well as truncated polypeptides consisting of nuclear targeting domain are rapidly taken up by cells and have biological effects (Green et al., 1988; Frankel et al., 1988). Since efficient cellular uptake is relevant for an anti-viral reagent, both modified and unmodified polypeptides are assayed for their ability to enter the cell. One method to evaluate cellular uptake is to label the polypeptides with a fluorescent dye, such as fluorescein isothiocyanate (FITC) (Pierce, Rockford, Ill.) at the single cysteine residue. The fluorescent-labeled polypeptides are added to the cell culture medium and the cellular distribution analyzed by fluorescence microscopy. For modified polypeptides, fluorescent labeling is carried out at a single cysteine residue before reacting amino groups with 2-iminothilane for attachment of the cleaving moiety. Alternatively, uptake of the reagent polypeptide can be evaluated using radioactive label since any polypeptide can be easily made radioactive during synthesis (Chen et al., 1986). Another alternative is to perform an immunofluorescence assay on fixed cells after incubation with the reagent using rabbit anti-peptide-antibodies and rhodamine-conjugated goat anti-rabbit antibodies (Malim et al., 1989).

The above methods to evaluate cellular uptake of an RNA-binding protein can be applied to any protein or polypeptide under investigation, e.g., TAT or REV. As has been demonstrated above, TAT covalently attached to the chemical cleaving group, 1,10-phenanthroline results in cleavage of target TAR sequences consistent with polypeptide binding to the 3-nt bulge. These results, along with existing evidence of the rapid cellular uptake of TAT polypeptides (Green et al., 1988; Frankel et al., 1988), suggest that chemical nucleases based on TAT may be useful for inactivating HIV mRNA in vivo.

In vivo cell systems allowing the expression of a selected RNA can be used to test the anti-viral effects of RNA-cleaving protein/peptide reagents. For example, the in vivo usefulness of the TAT24C-phen polypeptide is tested using a number of cell systems including the following:

(i) Chloramphenicol acetyltransferase (CAT) assays—HIV-1 LTR-directed CAT activity is measured under transient expression as well as stable expression conditions. For the transient assay, HeLa cells will be transfected with an expression vector containing the entire U3 region and 78 base pairs of the R region of the HIV LTR (e.g., pHIV-1LTR-CAT (S. Miller, SRI International, Menlo Park Calif.); or Gendelman et al., 1985). The LTR region contains the enhancer, promoter and TAR elements. Transfection is performed using the DEAE-dextran technique (Queen et al., 1983).

Twelve hours after transfection, the cells are incubated with the polypeptide reagent, over a range of polypeptide concentrations. Mitomycin C is added to the medium to induce CAT expression. Since the HIV-1 LTR is under the influence of NF-kB, the expression of CAT activity can be induced by treating with either UV or mitomycin C (Nabel et al., 1987). After 12 and 24 hours the cells are harvested and CAT activities are determined as described by Gorman et al. (1982). CAT activities are compared between (i) cell samples which were not treated with the polypeptide reagent, and (ii) cells samples which were treated with the polypeptide reagent. Cleavage of the target substrate by the polypeptide reagent is expected to result in a decrease of CAT activity. Polypeptide reagents containing phenanthrolene are complexed with $CuSO_4$ before addition to the cell samples.

If the cellular reduction potential is not sufficient for the cleavage to occur, ascorbic acid (or mercaptopropionic acid) is added to the medium.

To assess the activity of polypeptide reagents in the presence of wild-type TAT protein, a stable CAT expression system is used. HeLa cells are cotransfected with a 1:5 ratio of pSV2neo (a mammalian integration plasmid which confers neomycin-resistance; Southern et al., 1982) and pHIV-1LTR-CAT plasmids using DEAE-dextran procedure. Cells are selected for G418 resistance, and individual colonies are picked, expanded, and tested for CAT expression. CAT-active clones are transfected with a wild-type TAT expression vector (e.g., pcDEBtat, S. Miller, SRI International; or pAR, available from the AIDS Research and Reference Program). Cells now expressing TAT transiently are used for polypeptide treatment followed by the measurement of CAT activity.

The TAT24C-phen polypeptide reagent is added to the culture media over a range of concentrations. The ability of TAT24C-phen to block the transactivation by endogenous TAT protein is determined by measuring chloramphenicol acetyl transferase (CAT) activity over time after the addition of the TAT24C-phen polypeptide.

(ii) Chronically HIV-infected cell lines—The ability of TAT24C-phen to block induction of expression is also evaluated using chronically-HIV infected cell lines that produce HIV constitutively, e.g., ACH-2 (T-cells; Clouse et al., 1988), U1 (pro-monocytes; Folks et al., 1987), and H-9 cells. As above, the cells are treated using a range of polypeptide concentrations. Expression of HIV is monitored by one or more of the following standard methods:
  (a) HIV antigen levels, including p24, associated with HIV-infected cells (e.g., by ELISA (Wang et al., 1988, 1989; Crowe et al., 1990);
  (b) the reverse-transcriptase activity associated with HIV-infected cells; or
  (d) the level of replication of the HIV-I virus as identified by RNA transcription levels of the viral genome (e.g., slot-blot hybridization (Crowe et al., 1989)).
(iii) Blockincf acute infection—The ability of TAT24C-phen to prevent acute infection by HIV of the following cells will be assessed: PHA-stimulated human peripheral blood lymphocytes, MT4 and Jurkat cells (both CD4+ lymphocyte cell lines), macrophages, and monocytes infected by monocytropic HIV isolates.

In addition, cell toxicity of the TAT24C-phen polypeptide is evaluated using, for example, killing of Jurkat cells. Also, mutagenicity is evaluated with a standard Ames test.

For cleavage reactions carried out in cells in culture, the intracellular reduction potential can be modulated using N-acetyl cysteine, which increases the intracellular glutathione level (Roederer et al., 1990; Kalebic et al., 1991). Such manipulation of the intracellular reduction potential assist in keeping, for example, a copper atom of a cleaving agent in the reduced state.

RNA cleaving reagents composed of an RNA-binding protein and a non-specific nuclease also have important in vivo applications. A specific RNA cleaving-hybrid nuclease can be evaluated as described above when the hybrid nuclease is taken up into cells. Alternatively, CAT expression in Hela cells harboring target RNA-CAT fused genes are assayed in the presence and absence of hybrid-nuclease expressed from an independent promoter. For example, for expression in human cells, the gene for staphylococcal nuclease is cloned adjacent to the TAT or REV gene in plasmids pSV2TAT 72 (or pgTAT) and pCREV, respectively. The resultant plasmids encoding hybrid proteins are transfected into Hela cells carrying either pHIV-CAT or pHIV-env depending on the type of hybrid nuclease. The biological effects of the in vivo expression of TAT24C-nuclease is evaluated using the CAT assay as described above. The effect of the hybrid nuclease containing the gene product of REV will be assayed in Hela cells by quantitating the repression of the production of viral envelope protein as assayed using antibodies against envelope proteins.

Thus attaching staphylococcal nuclease to an RNA binding polypeptide (e.g., based on TAT and REV) using a short tether of several amino acids may generate a sequence-specific ribonuclease. Constitutive expression of such an RNA-specific nuclease in an un-infected cell, contained in a population of cells infected with an RNA virus that contains the target RNA binding sequence, may confer resistance of the un-infected cells against viral infection. For example, peripheral blood mononucleocyte cells are isolated from the blood of an HIV-positive patient. T-cells are isolated and transformed to carry a TAT-nuclease hybrid protein encoding gene. The cells are amplified and replaced in the patients blood stream. Such an approach may lead to a gene therapy for the treatment of AIDS: providing HIV-resistant T-cells.

Finally, a combined use of polypeptide-based RNA cleaving reagents combined with the above-described oligonucleotide cleaving agents may provide a two-pronged attack against viral diseases by providing cleavage of viral RNA and pro-viral DNA.

The following examples illustrate, but in no way are intended to limit the present invention.

Materials and Methods

General molecular genetic manipulations were carried out as described by Ausubel et al. and Sambrook et al. General manipulations involving protein/nucleic acid interactions are described in *Protein/DNA Interactions*, edited by Robert T. Sauer (Methods in Enzymology, Academic Press, 1991).

Synthetic oligonucleotide linkers and primers were prepared using commercially available automated oligonucleotide synthesizers. Alternatively, custom designed synthetic oligonucleotides may be purnchased, for example, from Synthetic Genetics (San Diego, Calif.).

Oligonucleotide sequences encoding peptides can be either synthesized directly by standard methods of oligonucleotide synthesis, or, in the case of large coding sequences, synthesized by a series of cloning steps involving a tandem array of multiple oligonucleotide fragments corresponding to the coding sequence (Crea; Yoshio et al.; Eaton et al.). Oligonucleotide coding sequences can be expressed by standard recombinant procedures (Sambrook et al.; Ausubel et al.)

Alternatively, peptides can be synthesized directly by standard in vitro techniques (Applied Biosystems, Foster City Calif.).

T7 RNA polymerase was purchased from Promega (Madison, Wis.) and used as per the manufacturer's instructions.

Polynucleotide kinase and restriction enzymes were obtained from Boehringer Mannheim (Indianapolis Ind.) or New England Biolabs (Beverly Mass.) and were used as per the manufacturer's directions.

Ribonuclease T1, Ribonuclease CL3, and S1 nuclease were obtained from Boehringer Mannheim and were used as per the manufacturer's directions. Uranyl nitrate was obtained from Mallencrodt (Paris Ky.).

Radionuclides were obtained from New England Nuclear (Boston, Mass.), ICN (Costa Mesa Calif.) or Amersham (Arlington Heights Ill.).

Mammalian, yeast, and bacterial expression vectors are commercially available from a number of sources including Bethesda Research Laboratories (Gaithersburg Md.) and Clontech (Palo Alto Calif.).

EXAMPLE 1

Preparation of TAT Protein and Derivative TAR-Binding Polypeptides

A. Preparation of the polypeptides.

The TAT and REV proteins are isolated as previously described (Weeks et al., 1990, herein incorporated by reference; Brown et al., 1990, herein incorporated by reference). The entire protein coding sequences of the TAT and REV proteins are presented in FIGS. 2A (SEQ ID NO:1) and 4 (SEQ ID NO:6), respectively. polypeptides derived from these proteins were synthesized at SRI's polypeptide synthesis facility using a Beckman model 990 polypeptide synthesizer, as per the manufacturer's instructions. Polypeptides having the same C-terminal sequence but truncated at different N-terminal sites are recovered from a single solid-phase synthesis by removing some of the reaction bed at different stages of the synthesis.

For the attachment of cleavage groups a cysteine residue can be added at any position internal to the polypeptide sequence or at either the amino- or carboxyterminal ends of the protein. The insertion of cysteine groups must be consistent with the maintenance of RNA-binding activity; such binding properties can be tested as described below.

The TAT polypeptide designated TAT24C was chemically synthesized as just described. TAT24C consists of amino acid residues 49–72 of the TAT protein (FIG. 2A, underlined sequence) and an additional cysteine residue at the C-terminus (FIG. 2B, SEQ ID NO:2). The TAT24C polypeptide was purified by standard HPLC.

B. Attachment of Nucleic Acid Cleaving Chemical Moieties.

Commercially available 5-nitro-1,10-phenanthroline (Sigma) is converted to 5-iodoacetamido-1,10-phenanthroline (Chen et al., 1986, herein incorporated by reference) (FIG. 5).

HPLC-purified cysteine-containing polypeptides are reacted with 5-iodoacetamido-1,10-phenanthroline to obtain polypeptides containing the phenantroline moiety (FIG. 2C) uniquely attached to the side chain of the cysteine residue contained in the polypeptide sequence (Chen et al., 1987, herein incorporated by reference).

After the addition of the phenanthroline moiety, the resulting polypeptides were separated from un-reacted iodo compound by passing the reaction mixtures through Sephadex G-50 spin columns (Pharmacia, Piscataway N.J.).

EXAMPLE 2

Preparation of RNA Substrates

The sequence of RNA target molecules were chosen based on previous studies characterizing the binding properties of the HIV-encoded TAT protein and the TAR target region from both HIV-1 and HIV-2: HIV-1 TAR is the 57-nt RNA stem-loop structure found in HIV-1 mRNA (nt 1–57); HIV-2 TAR includes the region of HIV-2 RNA essential for transactivation by HIV-2 TAT (nt 13–91, Arya et al., 1988); and ΔTAR is a truncated RNA containing the minimum TAT binding site (nt 17–43, Weeks et al., 1990 ). The three RNA substrates are shown in FIGS. 1A, 1B, and 1C. Further, the sequences of the RNA substrates are presented in the sequence listing as follows: HIV-1 TAR, SEQ ID NO:3; HIV-2 TAR, SEQ ID NO:4; and ΔTAR, SEQ ID NO:5.

The RNA substrates were synthesized as follows. Synthetic DNA templates were formed by standard phosphoramidate synthesis using a Model 381B synthesizer (Applied Biosystems, Foster City, Calif.). The synthetic DNA templates, containing T7 promoter sequences (Stahl et al., 1981; Davanloo et al., 1984) in addition to the RNA substrate sequences, were then used to generate uniformly labeled RNAs in vitro transcription of the synthetic DNA templates using T7 RNA polymerase (Milligan et al., 1987). In order to facilitate isolation of the newly generated RNA molecules, transcription was carried out in the presence of 32P-α-CTP (Amersham). The RNA molecules were purified by size fractionation on denaturing 10% polyacrylamide gels (Maniatis et al.; Sambrook et al.) followed by electroelution. The isolated RNA molecules were then heated to 70° C. and slowly cooled to room temperature to facilitate formation of the native secondary structure.

Further, both the wild-type RRE (WT-RRE) element (SEQ ID NO:23) and a truncated version of RRE (ΔRRE, SEQ ID NO:24) which contains the minimum domain (stem-loop II; Cook et al., 1991) of RRE, will be used. These RNAs are synthesized by in vitro transcription using T7 RNA polymerase as described above for TAR RNAS. WT-RRE can also be transcribed using a "BLUESCRIPT" plasmid (Stratagene, La Jolla, Calif.) carrying a 280 bp insert containing base pairs 7333-7612 of the RRE region (Daly et al., 1989). Transcribed RNAs are purified and end-labeled as described above.

EXAMPLE 3

Target Binding Assay

Approximately $10^3$ cpm of each uniformly labelled RNA substrate (Example 2) was incubated with either TAT24C or TAT24C-phen in a buffer containing 70 mM NaCl, 0.2 mM EDTA, 10 mM Tris-HCl (pH 7.5), 5% glycerol and 0.1% "NONIDET P40" (Sigma, St. Louis Mo.) for 20 minutes at 25° C. The samples were then run on a 10% native polyacrylamide gels in TBE (Tris-Borate-EDTA) buffer (Maniatis et al.; Sambrook, et al.) at room temperature. To obtain autoradiograms the gels were exposed to X-ray film. FIG. 3 shows a photograph of the resulting autoradiogram.

In FIG. 3, panel A, using HIV-1 TAR-RNA substrate: lane 1, in the presence of TAT24C (200 ng); lane 2, no polypeptide was added; lane 3, in the presence of TAT24C-phen (200 ng). In FIG. 3, panel B, using HIV-2 TAR-RNA substrate: lane 1, in the presence of TAT24C (200 ng); lane 2, no polypeptide was added; lane 3, in the presence of TAT24C-phen (200 ng). In FIG. 3, panel C, using ΔTAR-RNA as substrate: lane 1, no polypeptide was added; lane 2, in the presence of TAT24C-phen (200 ng). In FIG. 3, panel D, using yeast tRNA (Bethesda Research Laboratories, Gaithersburg Md.) as the substrate: lane 1, in the presence of TAT24C-phen (200 ng); lane 2, no protein was added; lanes 3 and 4 were with 200 ng and 400 ng of TAT24, respectively.

Discrete bands demonstrating retarded gel mobility were observed in samples containing both modified and unmodified polypeptides (FIG. 3A, lanes 1 and 3; FIG. 3B, lanes 1 and 3; and FIG. 3C, lane 2). These results show binding of polypeptides to all three RNAs containing the TAT responsive TAR element. The mobility shift of samples containing modified and unmodified polypeptides are virtually identical, indicating that the attachment of the phenanthroline moiety at the C-terminus of the polypeptide does not affect binding to the TAR site. There is no, or very low level, mobility shift with either polypeptide when tRNA was used as the substrate (FIG. 3D) indicating that the binding for TAR-containing RNA is specific.

EXAMPLE 4

Cleavage of TAR-Site Containing Substrates

A. Cleavage of HIV-1 TAR.

Cleavage reactions using the polypeptide-cleaving reagents of the present invention were typically performed as follows. RNA substrates were 5' end-labeled (Maniatis et al.; Sambrook, et al.) employing T4 polynucleotide kinase (Boehringer Mannheim) using $^{32}$P-γ-ATP (Amersham) and purified by gel electrophoresis as described above. Approximately 30 pmol of RNA was incubated in 10 μl of buffer A in the presence of TAT24C-phen, and cleavage was initiated by adding $CuSO_4$ (to a final concentration of 10 μM) and mercaptopropionic acid (to a final concentration of 2.5 mM) after 10 minutes at 22° C. After incubating for 17 hours, the reaction was stopped by adding the following to the indicated final concentrations: 2,9-dimethyl-1,10-phenanthroline to 3 mM, tRNA to 0.2 mg/ml, and sodium acetate (NaOAc) to 0.3 M. Typically 5' end-labeled, gel purified, HIV-1 TAR RNA ($10^3$ cpm) was used as the substrate in the following reactions.

In FIG. 8A, lane 1, RNA only; lane 2, TAT24C-phen (20 pmol); lane 3, TAT24C-phen (30 pmol); lane 4, S1 nuclease (1 U), incubated for 5 min at room temperature; lane 5, G-specific reaction, ribonuclease T1 (1 U), incubated for 10 min at 37° C. in 10 μl of buffer A (70 mM NaCl, 10 mM Tris-HCl (pH 7.5)); lane 6, C-specific reaction, ribonuclease CL3 (0.2 U), incubated for 20 min at 37° C. in 10 μl of buffer A; lane 7, cleavage at every nucleotide by irradiating RNA with 350-nm light (1.2 J in a "STRATALINKER", Stratagene, La Jolla, Calif.) at 25° C. in the presence of 20 mM uranyl nitrate; lane a, 40 μM Cu(II)-1,10-phenanthroline; lane b, TAT24C-phen (30 pmol) in the absence of Cu(II), same as lane 3 except that no $CuSO_4$ was added.

FIG. 8B presents fine mapping analysis of the cleavage sites at the 3' half of HIV-1 TAR. All reactions were conducted as described above. In FIG. 8B, lane 1, incubation with TAT24C-phen (90 ng); lane 2, incubation with TAT24C-phen (60 ng); lane 3, S1 cleavage; lane 4, uranyl nitrate cleavage; and lane 5, Ribonuclease CL3 digestion. FIG. 8B represents a gel subjected to longer electrophoresis time in order to separate larger fragments.

RNAs from all reactions were ethanol precipitated and analyzed on a denaturing (8.3 M urea) 15% polyacrylamide gel. The gel was dried and autoradiographed.

A summary of the cleavage sites on HIV-1 TAR RNA are indicated by arrows in the RNA structure shown between FIGS. 8A and 8B.

B. Cleavage of HIV-1 ΔTAR RNA.

Cleavage reactions were carried out as above except that 5' end-labeled, gel purified, ΔTAR RNA ($10^3$ cpm) was used as the substrate for the following reactions. FIG. 8B, lane 1, cleavage with Cu(II)-1,10-phenanthroline; lane 2, Uranyl nitrate ladder; lane 3, S1 cleavage; lane 4, RNA only; lanes 5 and 6, TAT24C-phen cleavage (20 pmol, lane 5 and 30 pmol, lane 6).

As above, RNAs from all reactions were ethanol precipitated and analyzed on a denaturing (8.3 M urea) 15% polyacrylamide gel. The gel was dried and autoradiographed.

A summary of the cleavage sites on ΔTAR RNA are indicated by arrows in FIG. 8C.

C. Cleavage of HIV-2 TAR RNA.

Cleavage reactions were performed as described above except that 5' end-labeled, gel purified HIV-2 TAR RNA ($10^3$ cpm) was used as substrate for the following reactions. In FIG. 9A, lane 1, TAT24C-phen (30 pmol); lane 2, TAT24C-phen (20 pmol); lane 3, RNA only; lane 4, S1 nuclease; lane 5, uranyl nitrate ladder; lane 6, C-specific reaction; lane 7, G-specific reaction.

RNAs from all reactions were ethanol precipitated and analyzed on a denaturing (8.3 M urea) 15% polyacrylamide gel. The gel was dried and autoradiographed. The cleavage sites on the HIV-2 TAR RNA are indicated by arrows.

D. Cleavage of tRNA.

Figure 9B:
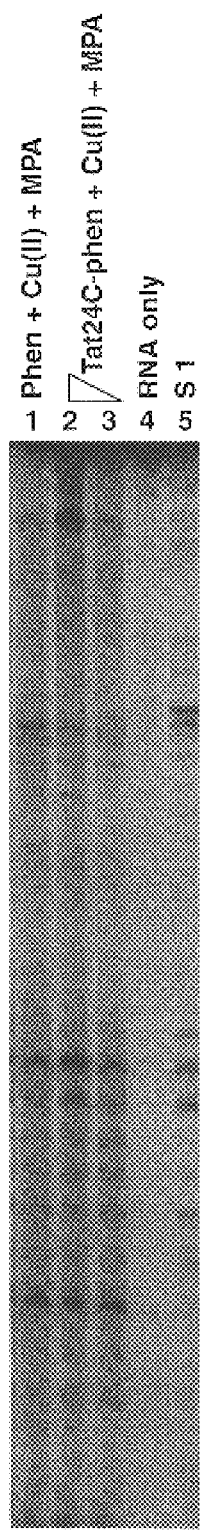
FIG. 9B shows the cleavage products resulting from using tRNA as a substrate RNA.

Cleavage reactions were performed as described above except that 5' end-labeled, gel purified tRNA (yeast tRNA; Bethesda Research Laboratories, Gaithersburg Md.) ($10^3$ cpm) was used as substrate for the following reactions. In FIG. 9B, lane 1, Cu(II)-1,10-phenanthroline (40 mM); lane 2, TAT24C-phen (60 pmol); lane 3, TAT24C-phen (30 pmol); lane 4, RNA only; lane 5, S1 nuclease.

RNAs from all reactions were ethanol precipitated and analyzed on a denaturing (8.3 M urea) 15% polyacrylamide gel. The gel was dried and autoradiographed.

E. Analysis of Cleavage Results.

The chemical nuclease activity of Cu(II)-complexed 1,10-phenanthroline derives from an oxidative attack on the sugar ring by a copper-oxo species generated in the presence of a reducing agent (Sigman et al., 1990). The nucleolytic activity of TAT24C-phen on HIV-1 TAR is shown in FIG. 8A. As seen in lanes 2 and 3, cleavage occurs primarily in the loop of the target RNA (structure shown between FIGS. 8A and 8B), especially at the uridine ($U_{30}$) in the 5' side of the loop.

A secondary cleavage site can also be seen on the stem, at nt 12–14 and 18 (indicated by the short arrows in the RNA structure shown in FIG. 8A) and at nt 43–45 on the complementary region (FIG. 8B). The cleavage pattern on opposite sides of the stem is shifted to the 5' side, an indication that the cleaving moiety is occupying the major groove of the duplex RNA stem (Dervan, 1986; Sluka et al., 1987). A possible alternative binding mode, where the basic region of TAT24C-phen polypeptide binds to the minor groove and the phenanthroline moiety reaches over to the major groove to effect cleavage, is unlikely based on evidence suggesting that TAT-derived polypeptides bind in the major groove (Weeks et al., 1991). Further, binding of the TAT24C-phen polypeptide to the minor grove is unlikely since, at least in the case of B-DNA, Cu(II)-1,10-phenanthroline prefers to bind to the minor groove (Sigman et al., 1990). Overall, the cleavage sites lie on either side of the bulge where the TAT protein is known to bind to the TAR target site ( Roy et al., 1990; Cordingley et al., 1990; Dingwall et al., 1989; Weeks et al., 1990). Because Cu(II)-phenanthroline is known to preferentially cleave unpaired bases of RNA (Murakawa et al., 1989), HIV-1 TAR was incubated with free Cu(II)-1,10-phenanthroline, i.e., not bound to RNA-binding protein, as a control. As shown in lane A (FIG. 8A), free phenanthroline cleaves everywhere, but the unpaired bases at the loop (especially $G_{32}$) and the bulge are most reactive. Thus, tethering phenanthroline to the polypeptide suppresses non-specific cleavage on TAR RNA.

In the absence of cupric ions, TAT24C-phen produces no cleavage (lane B, FIG. 8A).

The cleavage pattern on ΔTAR, which lacks the base of the stem, is consistent with that of full-length TAR (FIG. 8C), suggesting that the minimum TAT binding site is sufficient to be recognized by TAT24C-phen. Using the ΔTAR substrate, the cleavage is restricted to the loop, but the pattern is very different from that for cleavage by free phenanthroline (compare lane 1 with lanes 5 and 6 of FIG. 8C).

In contrast to cleavage of HIV-1 TAR, for which the primary site is at the loop adjacent to the TAT binding site, cleavage of HIV-2 TAR takes place mainly at the stem, roughly midway between the two loops (FIG. 9A, lanes 1 and 2). HIV-2 TAR has two 2-nt bulges, both of which have the consensus TAT binding motif (Weeks et al., 1990; Green et al., 1988; Frankel et al., 1988; Milligan et al., 1987; Arya et al., 1988; Weeks et al., 1991; Murakawa et al., 1989). HIV-1 TAT can transactivate HIV-2 LTR-directed gene expression when either stem-loop I or stem-loop II is present (although the TAT product of HIV-2 requires both stem-loops for efficient transactivation (Arya et al., 1988; Emerman et al., 1987). Accordingly, the HIV-1 encoded TAT protein appears to bind to either stem-loop. Because the TAT24C polypeptide is based on HIV-1 TAT, the cleavage of both loops probably results from binding of the polypeptide to both elements. The major cleavage site for HIV-2 thus corresponds to the minor cleavage site for HIV-1 TAR (i.e., approximately 3–8 base pairs from the bulge in the direction away from the loop(s)). The higher level of cleavage at this site could be partly due to a superimposition of the cleavage resulting from TAT24C-phen binding on both stem-loops I and II. Alternatively, TAT24C-phen might bind only to stem-loop I and the molecule could fold to bring the two loops close together.

When tRNA was used as the substrate for cleavage, the cleavage pattern induced by TAT24C-phen was identical with that caused by free Cu(II)-phenanthroline (FIG. 9B), indicating that TAT24C-phen does not induce site-specific cleavage on RNA lacking a TAR site.

In the absence of the reducing agent mercaptopropionic acid, Cu(II)-complexed TAT24C-phen still cleaves TAR-containing RNA, presumably via a Cu+2-induced hydrolytic pathway (Modak et al., 1991) but with lower efficiency. When mercaptopropionic acid was replaced by ascorbic acid, a reducing agent more suitable for in vivo studies, the rate of cleavage increased.

While the invention has been described with reference to specific methods and embodiments, it will be appreciated that various modifications and changes may be made without departing from the invention.

It is claimed:

1. A viral polypeptide having site-specific viral-RNA binding, where said polypeptide is modified to contain a moiety capable of cleaving an RNA backbone.

2. The polypeptide of claim 1, wherein said polypeptide is selected from the group consisting of polypeptides having the amino acid sequences presented as SEQ ID NO:1, SEQ ID NO:2, SEQ ID NO:6, SEQ ID NO:7 and SEQ ID NO:22.

3. The polypeptide of claim 1, wherein said moiety is selected from the group consisting of phenanthroline Cu(II), Zn(II), Fe(II)-EDTA, Cu(II)-bipyridine, and Cu(II)-terpyridine.

4. The polypeptide of claim 2, wherein the polypeptide has the sequence presented as SEQ ID NO:1, which further contains an end-terminal cysteine residue, and the moiety is phenanthroline.

5. The polypeptide of claim 2, wherein the polypeptide has the sequence presented as SEQ ID NO:2 and the moiety is phenanthroline.

6. The polypeptide of claim 2, wherein said moiety is a non-specific nuclease.

7. The polypeptide of claim 6, wherein the polypeptide has the sequence presented as SEQ ID NO:2 and the non-specific nuclease is Staphylococcal nuclease.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 86 amino acids
      (B) TYPE: amino acid
      (D) TOPOLOGY: linear (ii) MOLECULE TYPE: protein (iii) HYPOTHETICAL: NO (iv) ANTI-SENSE: NO (vi) ORIGINAL SOURCE:
      (C) INDIVIDUAL ISOLATE: the sequence of the TAT protein of
         HIV-1

(xi) SEQUENCE DESCRIPTION: SEQ ID NO:1:

```
Met Glu Pro Val Asp Pro Arg Leu Glu Pro Trp Lys His Pro Gly Ser
1               5                  10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85
```

(2) INFORMATION FOR SEQ ID NO:2:

(i) SEQUENCE CHARACTERISTICS:
      (A) LENGTH: 25 amino acids
      (B) TYPE: amino acid
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (C) INDIVIDUAL ISOLATE: the sequence of the TAT24C peptide (xi) SEQUENCE DESCRIPTION: SEQ ID NO:2:

Arg Lys Lys Arg Arg Gln Arg Arg Arg Pro Pro Gln Gly Ser Gln Thr
1               5                  10                  15

His Gln Val Ser Leu Ser Lys Gln Cys
            20                  25

(2) INFORMATION FOR SEQ ID NO:3:

(i) SEQUENCE CHARACTERISTICS:
             (A) LENGTH: 58 base pairs
             (B) TYPE: nucleic acid
             (C) STRANDEDNESS: both
             (D) TOPOLOGY: linear (ii) MOLECULE TYPE: RNA (genomic)

(iii) HYPOTHETICAL: NO (iv) ANTI-SENSE: NO (vi) ORIGINAL SOURCE:
             (C) INDIVIDUAL ISOLATE: the sequence of the TAR site of
                 HIV-1

(xi) SEQUENCE DESCRIPTION: SEQ ID NO:3:

GGUCUCUCUG GUUAGACCAG AUCUGAGCCU GGGAGCUCUC UGGCUAACUA GAGAACCC          58

(2) INFORMATION FOR SEQ ID NO:4:

(i) SEQUENCE CHARACTERISTICS:
             (A) LENGTH: 77 base pairs
             (B) TYPE: nucleic acid
             (C) STRANDEDNESS: both
             (D) TOPOLOGY: linear (ii) MOLECULE TYPE: RNA (genomic)

(iii) HYPOTHETICAL: NO (iv) ANTI-SENSE: NO (vi) ORIGINAL SOURCE:
             (C) INDIVIDUAL ISOLATE: the sequence of the TAR site of
                 HIV-2

(xi) SEQUENCE DESCRIPTION: SEQ ID NO:4:

GGGAGGCUGG CAGAUUGAGC CCUGGGAGGU UCUCUCCAGC CUAGCAGGUA GAGCCUGGGU          60

GUUCCCUGCU AGCUCCC                                                        77

(2) INFORMATION FOR SEQ ID NO:5:

(i) SEQUENCE CHARACTERISTICS:
             (A) LENGTH: 27 base pairs
             (B) TYPE: nucleic acid
             (C) STRANDEDNESS: both
             (D) TOPOLOGY: linear (ii) MOLECULE TYPE: RNA (genomic)

```
    (iii) HYPOTHETICAL: NO (iv) ANTI-SENSE: NO (vi) ORIGINAL SOURCE:
         (C) INDIVIDUAL ISOLATE: the sequence of a truncated TAR site
             of HIV-1

(xi) SEQUENCE DESCRIPTION: SEQ ID NO:5:

GCAGAUCUGA GCCUGGGAGC UCUCUGC                                                27

(2) INFORMATION FOR SEQ ID NO:6:

(i) SEQUENCE CHARACTERISTICS:
        (A) LENGTH: 116 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
         (C) INDIVIDUAL ISOLATE: the sequence of the REV protein of
             HIV-1

(xi) SEQUENCE DESCRIPTION: SEQ ID NO:6:

Met Ala Gly Arg Ser Gly Asp Ser Asp Glu Asp Leu Leu Lys Ala Val
1               5                   10                  15

Arg Leu Ile Lys Phe Leu Tyr Gln Ser Asn Pro Pro Asn Pro Glu
            20                  25                  30

Gly Thr Arg Gln Ala Arg Arg Asn Arg Arg Arg Trp Arg Glu Arg
        35                  40                  45

Gln Arg Gln Ile His Ser Ile Ser Glu Arg Ile Leu Ser Thr Tyr Leu
    50                  55                  60

Gly Arg Ser Ala Glu Pro Val Pro Leu Gln Leu Pro Pro Leu Glu Arg
65                  70                  75                  80

Leu Thr Leu Asp Cys Asn Glu Asp Cys Gly Thr Ser Gly Thr Gln Gly
                85                  90                  95

Val Gly Ser Pro Gln Ile Leu Val Glu Ser Pro Thr Ile Leu Glu Ser
            100                 105                 110

Gly Ala Lys Glu
        115

(2) INFORMATION FOR SEQ ID NO:7:

(i) SEQUENCE CHARACTERISTICS:
        (A) LENGTH: 48 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
         (C) INDIVIDUAL ISOLATE: a peptide derived from the REV
             protein of HIV-1

(xi) SEQUENCE DESCRIPTION: SEQ ID NO:7:

Leu Ile Lys Phe Leu Tyr Gln Ser Asn Pro Pro Asn Pro Glu Gly
```

```
            1               5                   10                  15
        Thr Arg Gln Ala Arg Arg Asn Arg Arg Arg Arg Trp Arg Glu Arg Gln
                        20                  25                  30

Arg Gln Ile His Ser Ile Ser Glu Arg Ile Leu Ser Thr Tyr Leu Gly
                    35                  40                  45
```

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: HIV-LTR TARGET REGION, 11A (xi) SEQUENCE DESCRIPTION: SEQ ID NO:8:

TTTAAAAGAA AAGGGGGGAC TGG        23

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: HIV-LTR TARGET REGION, 11B (xi) SEQUENCE DESCRIPTION: SEQ ID NO:9:

GCTGGGACTT TCCAGGGAGG CGT        23

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: HIV-LTR TARGET REGION, 11C (xi) SEQUENCE DESCRIPTION: SEQ ID NO:10:

CCTGGGCGGG ACTGGGAGT GGCGAGCCC        29

(2) INFORMATION FOR SEQ ID NO:11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
            (C) INDIVIDUAL ISOLATE: SINGLE STRAND OLIGONUCLEOTIDE, 12/A1

(xi) SEQUENCE DESCRIPTION: SEQ ID NO:11:

AGGGGGGAAA AGAAAA                                                        16

(2) INFORMATION FOR SEQ ID NO:12:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (vi) ORIGINAL SOURCE:
            (C) INDIVIDUAL ISOLATE: SINGLE STRAND OLIGONUCLEOTIDE,
                12/A-2

(xi) SEQUENCE DESCRIPTION: SEQ ID NO:12:

TTTTCTTTTC CCCCCT                                                        16

(2) INFORMATION FOR SEQ ID NO:13:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (vi) ORIGINAL SOURCE:
            (C) INDIVIDUAL ISOLATE: SINGLE STRAND OLIGONUCLEOTIDE,
                12/B-1

(xi) SEQUENCE DESCRIPTION: SEQ ID NO:13:

GGAGGGACCT TTCAGGGG                                                      18

(2) INFORMATION FOR SEQ ID NO:14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (vi) ORIGINAL SOURCE:
            (C) INDIVIDUAL ISOLATE: SINGLE STRAND OLIGONUCLEOTIDE,
                12/B-2

(xi) SEQUENCE DESCRIPTION: SEQ ID NO:14:

CCCCTGAAAG GTCCCTCC                                                      18

(2) INFORMATION FOR SEQ ID NO:15:

(i) SEQUENCE CHARACTERISTICS:
            (A) LENGTH: 23 base pairs
            (B) TYPE: nucleic acid
            (C) STRANDEDNESS: single (D) TOPOLOGY: linear (ii) MOLECULE TYPE: DNA (genomic)

(iii) HYPOTHETICAL: NO (vi) ORIGINAL SOURCE:
            (C) INDIVIDUAL ISOLATE: SINGLE STRAND OLIGONUCLEOTIDE,
                12/C-1

(xi) SEQUENCE DESCRIPTION: SEQ ID NO:15:

GAGGGGAGAG GGGAGAGGGG GGG                                              23

(2) INFORMATION FOR SEQ ID NO:16:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (vi) ORIGINAL SOURCE:
            (C) INDIVIDUAL ISOLATE: SINGLE STRAND OLIGONUCLEOTIDE,
                12/C-2

(xi) SEQUENCE DESCRIPTION: SEQ ID NO:16:

CCCGCCCTGA CCCCTCACCG CTC                                              23

(2) INFORMATION FOR SEQ ID NO:17:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (vi) ORIGINAL SOURCE:
            (C) INDIVIDUAL ISOLATE: SINGLE STRAND OLIGONUCLEOTIDE, 12/K (xi) SEQUENCE DESCRIPTION: SEQ ID NO:17:

AAAAGAAAAG GGGGA                                                       16

(2) INFORMATION FOR SEQ ID NO:18:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (vi) ORIGINAL SOURCE:
            (C) INDIVIDUAL ISOLATE: SINGLE STRAND OLIGONUCLEOTIDE, 12/L (xi) SEQUENCE DESCRIPTION: SEQ ID NO:18:

GGGGATCCCT TAGGGAGG                                                    18

(2) INFORMATION FOR SEQ ID NO:19:

(i) SEQUENCE CHARACTERISTICS:

(A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: SINGLE STRAND OLIGONUCLEOTIDE, 12/M (xi) SEQUENCE DESCRIPTION: SEQ ID NO:19:

GGGTGGGATC GGGGAGCGGT GGAGAG                                              26

(2) INFORMATION FOR SEQ ID NO:20:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: SINGLE STRAND OLIGONUCLEOTIDE,
            FIGURE 13

(ix) FEATURE:
        (A) NAME/KEY: modified_base
        (B) LOCATION: 25..29
        (D) OTHER INFORMATION: /mod_base= OTHER
            /note= "WHERE N=ABASIC RESIDUE"

(xi) SEQUENCE DESCRIPTION: SEQ ID NO:20:

TCTTCTCCTC CTTTTTTCCT TTTTNNNNNT TTTTCCTTTT TTCCTCCTCT TCT               53

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (vi) ORIGINAL SOURCE:
        (C) INDIVIDUAL ISOLATE: TARGET RNA, FIGURE 13

(xi) SEQUENCE DESCRIPTION: SEQ ID NO:21:

GGUAGAAGAG GAGGAAAAAA GGAAAAACUG                                          30

(2) INFORMATION FOR SEQ ID NO:22:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (C) INDIVIDUAL ISOLATE: polypeptide containing the basic -continued domain of HIV-REV protein (xi) SEQUENCE DESCRIPTION: SEQ ID NO:22:

Thr Arg Gln Ala Arg Arg Asn Arg Arg Arg Arg Trp Arg Glu Arg Gln
1               5                   10                  15

Arg (2) INFORMATION FOR SEQ ID NO:23:

(i) SEQUENCE CHARACTERISTICS:
        (A) LENGTH: 244 base pairs
        (B) TYPE: nucleic acid
        (C) STRANDEDNESS: both
        (D) TOPOLOGY: linear (ii) MOLECULE TYPE: RNA (genomic)

(iii) HYPOTHETICAL: NO (vi) ORIGINAL SOURCE:
        (C) INDIVIDUAL ISOLATE: HIV-1 REV RESPONSE ELEMENT, FIGURE
            14

(xi) SEQUENCE DESCRIPTION: SEQ ID NO:23:

CAGUGGGAAU AGGAGCUUUG UUCCUUGGGU UCUUGGGAGC AGCAGGAAGC ACUAUGGGCG      60

CAGCGUCAAU GACGCUGACG GUACAGGCCA GACAAUUAUU GUCUGGUAUA GUGCAGCAGC     120

AGAACAAUUU GCUGAGGGCU AUUGAGGCGC AACAGCAUCU GUUGCAACUC ACAGUCUGGG    180

GCAUCAAGCA GCUCCAGGCA AGAAUCCUGG CUGUGGAAAG AUACCUAAAG GAUCAACAGC    240

UCCU                                                                  244

(2) INFORMATION FOR SEQ ID NO:24:

(i) SEQUENCE CHARACTERISTICS:
        (A) LENGTH: 69 base pairs
        (B) TYPE: nucleic acid
        (C) STRANDEDNESS: both
        (D) TOPOLOGY: linear (ii) MOLECULE TYPE: RNA (genomic)

(iii) HYPOTHETICAL: NO (vi) ORIGINAL SOURCE:
        (C) INDIVIDUAL ISOLATE: STEM II OF THE HIV-1 REV RESPONSE
            ELEMENT, FIGURE 14

(xi) SEQUENCE DESCRIPTION: SEQ ID NO:24:

AGCACUAUGG GCGCAGCGUC AAUGACGCUG ACGGUACAGG CCAGACAAUU AUUGUCUGGU     60

AUAGUGCAG                                                             69